(12) United States Patent
Reznicek et al.

(10) Patent No.: US 11,439,361 B2
(45) Date of Patent: Sep. 13, 2022

(54) METHODS AND SYSTEMS FOR MEDICAL IMAGING VIBRATION REDUCTION

(71) Applicant: GE Precision Healthcare LLC, Milwaukee, WI (US)

(72) Inventors: Mark Reznicek, Sussex, WI (US); Chad Allan Smith, Franklin, WI (US); Charles Smith, Sussex, WI (US); James Kluth, Waukesha, WI (US)

(73) Assignee: GE Precision Healthcare LLC, Milwaukee, WI (US)

( * ) Notice: Subject to any disclaimer, the term of this patent is extended or adjusted under 35 U.S.C. 154(b) by 190 days.

(21) Appl. No.: 16/775,978

(22) Filed: Jan. 29, 2020

(65) Prior Publication Data

US 2021/0228172 A1 Jul. 29, 2021

(51) Int. Cl.
*G01N 23/04* (2018.01)
*A61B 6/00* (2006.01)
(Continued)

(52) U.S. Cl.
CPC ............ *A61B 6/5264* (2013.01); *A61B 6/032* (2013.01); *A61B 6/0487* (2020.08);
(Continued)

(58) Field of Classification Search
CPC ..... A61B 6/032; A61B 6/0487; A61B 6/4411; A61B 6/4447; A61B 6/484; A61B 6/5264; A61B 17/00234; A61B 17/0218; A61B 17/16; A61B 17/1615; A61B 17/162; A61B 17/1622; A61B 17/1624; A61B 17/1626; A61B 17/1666; A61B 17/1675; A61B 17/1703; A61B 17/1746; A61B 17/32002; A61B 17/3403; A61B 17/3423; A61B 2017/00199; A61B 2017/00398; A61B 6/035; A61B 6/0407; A61B 6/4007; A61B 6/4452; A61B 6/54; A61B 6/5211; A61B 6/4266; A61B 6/4085; A61B 6/06; H01J 2235/1093; H01J 35/02; H01L 2924/00; H01L 2224/48091; H01L 2924/01015; H01L 2924/01047; H01L 2924/1305; H01L 2924/13091; H01L 2924/1461; H01L 2924/181; H01L 2924/30107;
(Continued)

(56) References Cited

U.S. PATENT DOCUMENTS

| 2001/0022515 A1* | 9/2001 | Yamashita ......... G01R 33/3854 324/300 |
| 2001/0024320 A1* | 9/2001 | Okada .................... G02B 21/24 359/368 |

(Continued)

*Primary Examiner* — Irakli Kiknadze
(74) *Attorney, Agent, or Firm* — McCoy Russell LLP

(57) ABSTRACT

Various methods and systems are provided for reducing vibration in a rotating body of a medical imaging system. In an example, a dynamic vibration absorber (DVA) for a medical imaging system includes a mount portion including one or more apertures and adapted to fixedly couple to a mount surface within the imaging system; a sprung portion; and a vibrational tuner, where when the mount portion is mounted to the mount surface and during operation of the imaging system, the sprung portion moves relative to the mount surface, an amount of movement of the sprung portion based at least in part on the vibrational tuner.

20 Claims, 9 Drawing Sheets

(51) Int. Cl.
*A61B 6/03* (2006.01)
*H01J 35/02* (2006.01)
*A61B 6/04* (2006.01)

(52) U.S. Cl.
CPC .......... *A61B 6/4411* (2013.01); *A61B 6/4447* (2013.01); *A61B 6/484* (2013.01); *H01J 35/02* (2013.01); *H01J 2235/1093* (2013.01)

(58) Field of Classification Search
CPC ..... H01L 2924/3011; H01L 2924/3025; H01L 2924/00012; H01L 2924/00014; H01L 2224/48247; H01L 23/53285; H01L 31/032; H01L 31/078; H01L 31/024; H05G 1/02; G01J 5/044; G01J 5/061; G01V 1/201; F16F 15/022; G01R 33/3854; G03B 1/42; G03B 21/113
USPC .............................. 359/368; 324/300; 378/62
See application file for complete search history.

(56) References Cited

U.S. PATENT DOCUMENTS

| | | | |
|---|---|---|---|
| 2014/0192956 A1* | 7/2014 | Kim ..................... | A61B 6/4429 378/62 |
| 2019/0150878 A1* | 5/2019 | Smith .................. | A61B 6/5205 |

* cited by examiner

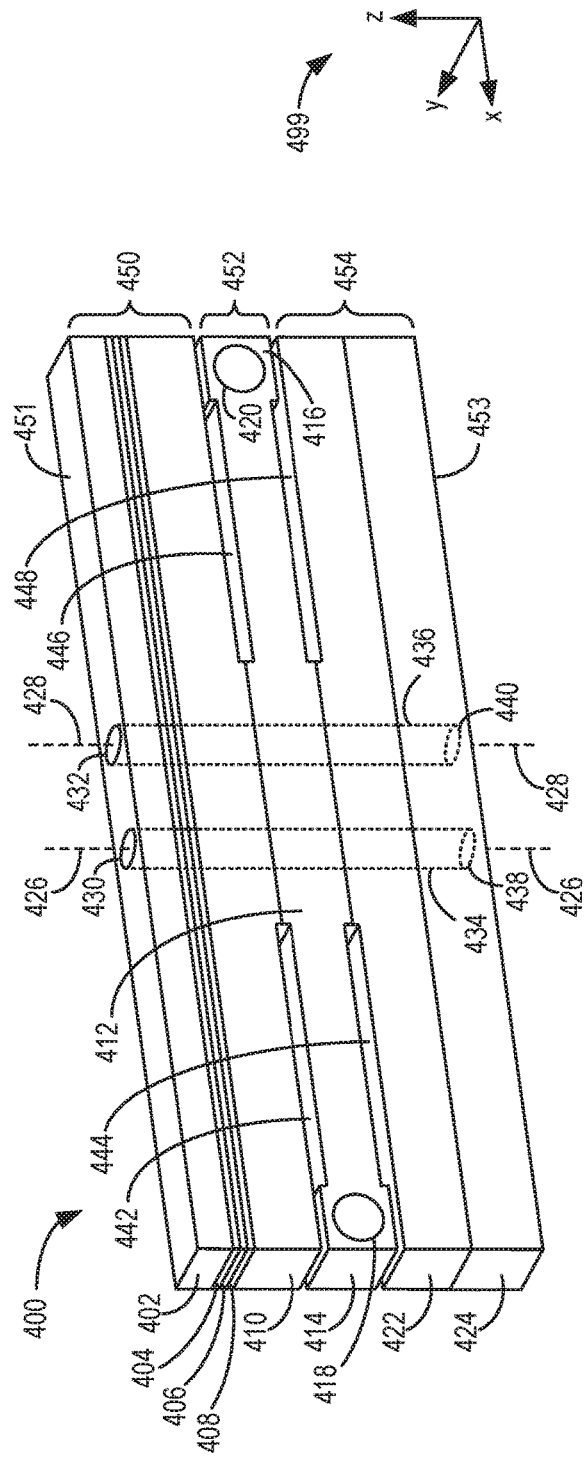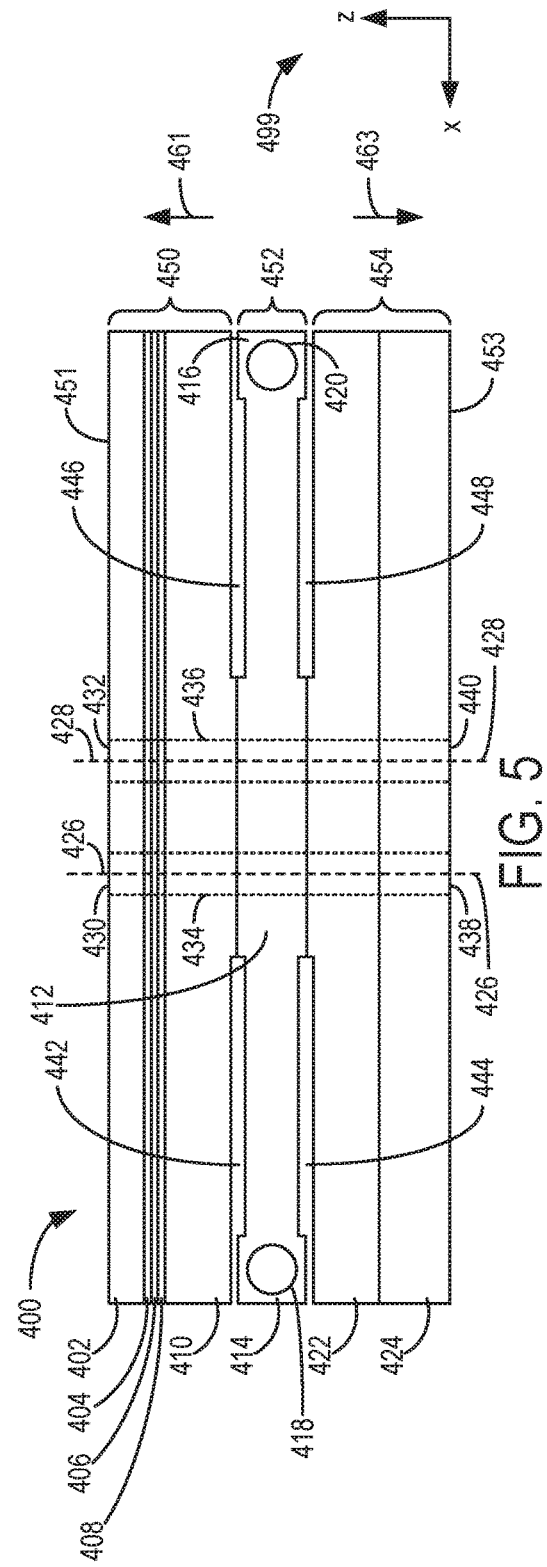

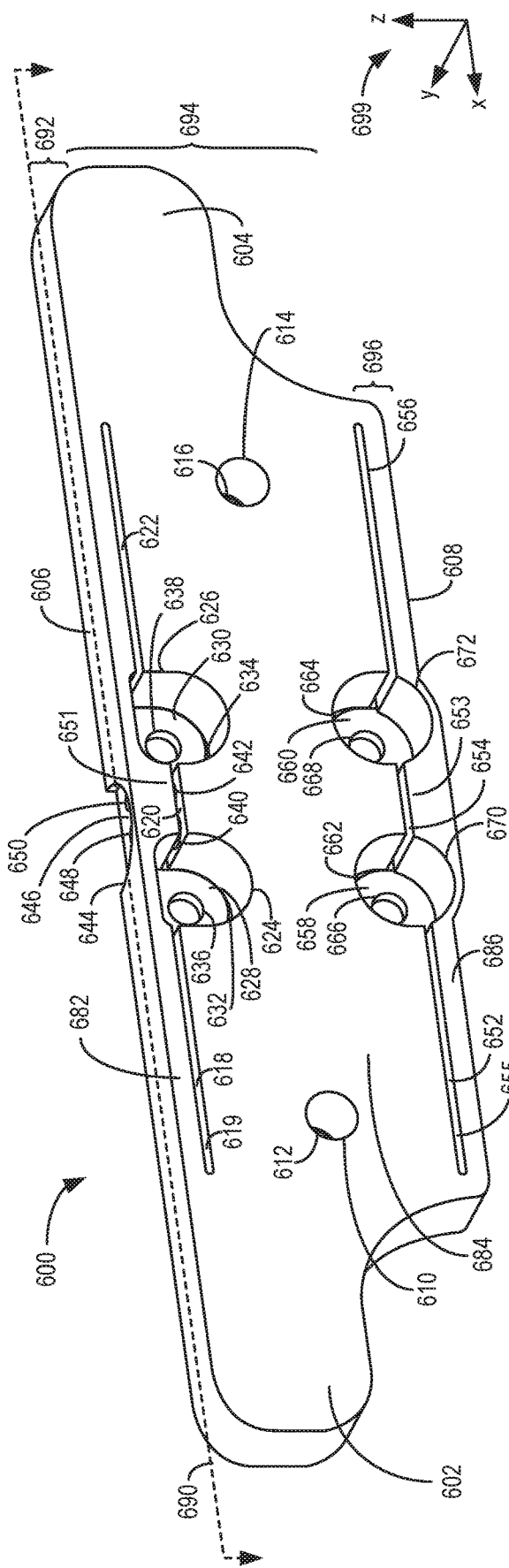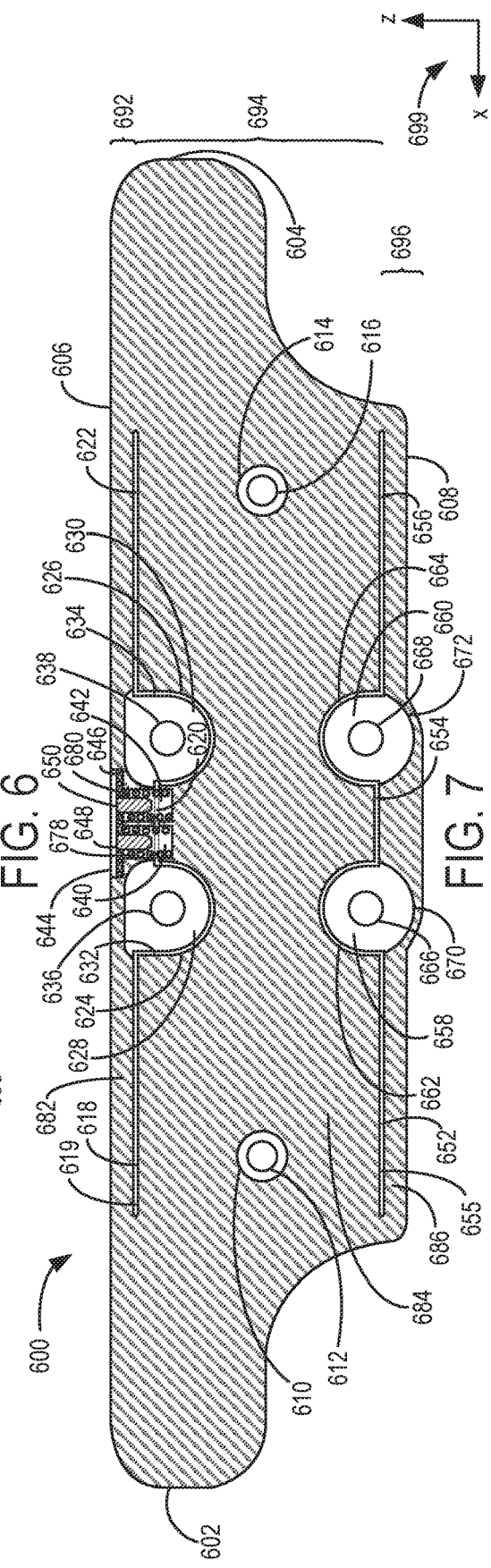

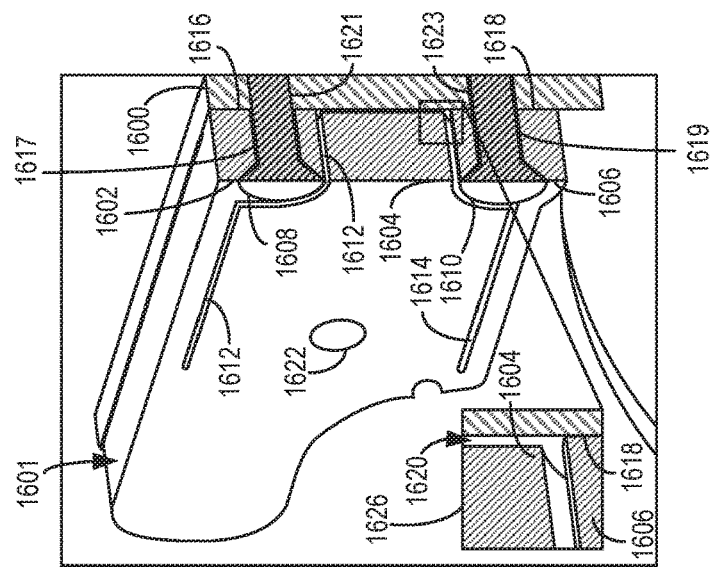
FIG. 18
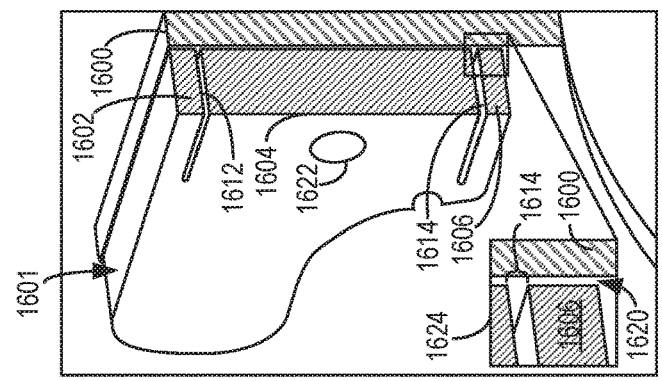
FIG. 17
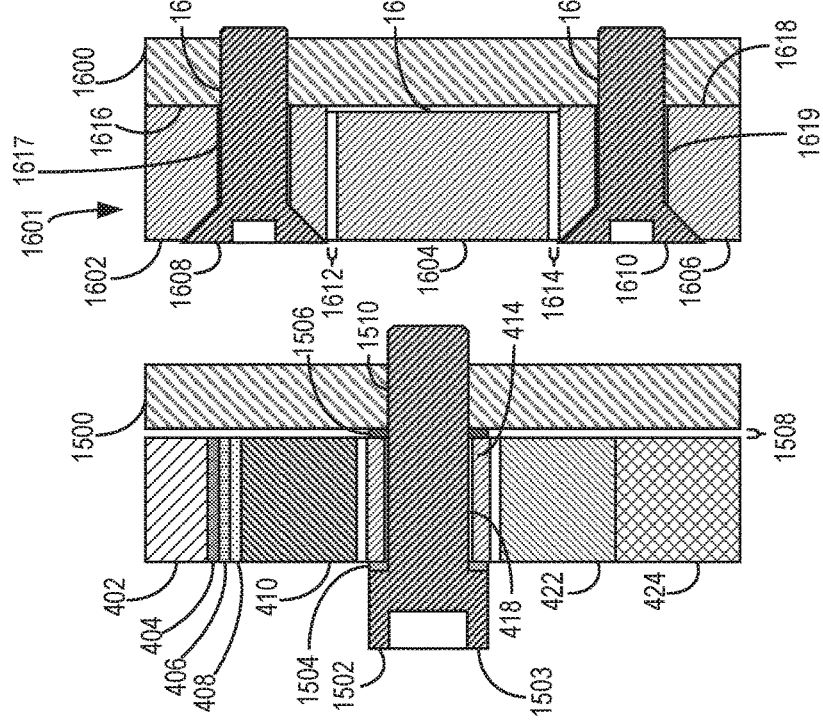
FIG. 16
FIG. 15

METHODS AND SYSTEMS FOR MEDICAL IMAGING VIBRATION REDUCTION

FIELD

Embodiments of the subject matter disclosed herein relate to medical imaging, and more particularly, to computed tomography (CT) medical imaging.

BACKGROUND

Non-invasive imaging technologies allow images of the internal structures of a patient or object to be obtained without performing an invasive procedure on the patient or object. In particular, technologies such as computed tomography (CT) use various physical principles, such as the differential transmission of x-rays through the target volume, to acquire image data and to construct tomographic images (e.g., three-dimensional representations of the interior of the human body or of other imaged structures). CT scanners may include a rotatable gantry on which an x-ray radiation source and x-ray radiation detectors are mounted. The vibration of the gantry as it rotates directly translates to degradation in image quality, as gantry vibration can distort images and create streaks/artifacts in the patient data.

BRIEF DESCRIPTION

In one embodiment, a dynamic vibration absorber (DVA) for a medical imaging system includes a mount portion including one or more apertures and adapted to fixedly couple to a mount surface within the imaging system; a sprung portion; and a vibrational tuner, where when the mount portion is mounted to the mount surface and during operation of the imaging system, the sprung portion moves relative to the mount surface, an amount of movement of the sprung portion based at least in part on the vibrational tuner.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present disclosure will be better understood from reading the following description of non-limiting embodiments, with reference to the attached drawings, wherein below:

FIG. 4 shows a perspective view of a dynamic vibration absorber according to an embodiment.

FIG. 5 shows an end view of the dynamic vibration absorber of FIG. 4.

FIG. 6 shows a perspective view of a dynamic vibration absorber according to an embodiment.

FIG. 7 shows a cross-sectional view of the dynamic vibration absorber of FIG. 6.

FIG. 15 shows a cross-section view of the dynamic vibration absorber of FIGS. 4-5.

FIGS. 16-18 show different cross-sectional views of the dynamic vibration absorber of FIGS. 6-8.

FIGS. 4-8, 13, and 15-18 are shown to scale, although other relative dimensions may be used, if desired.

DETAILED DESCRIPTION

Figure 8:
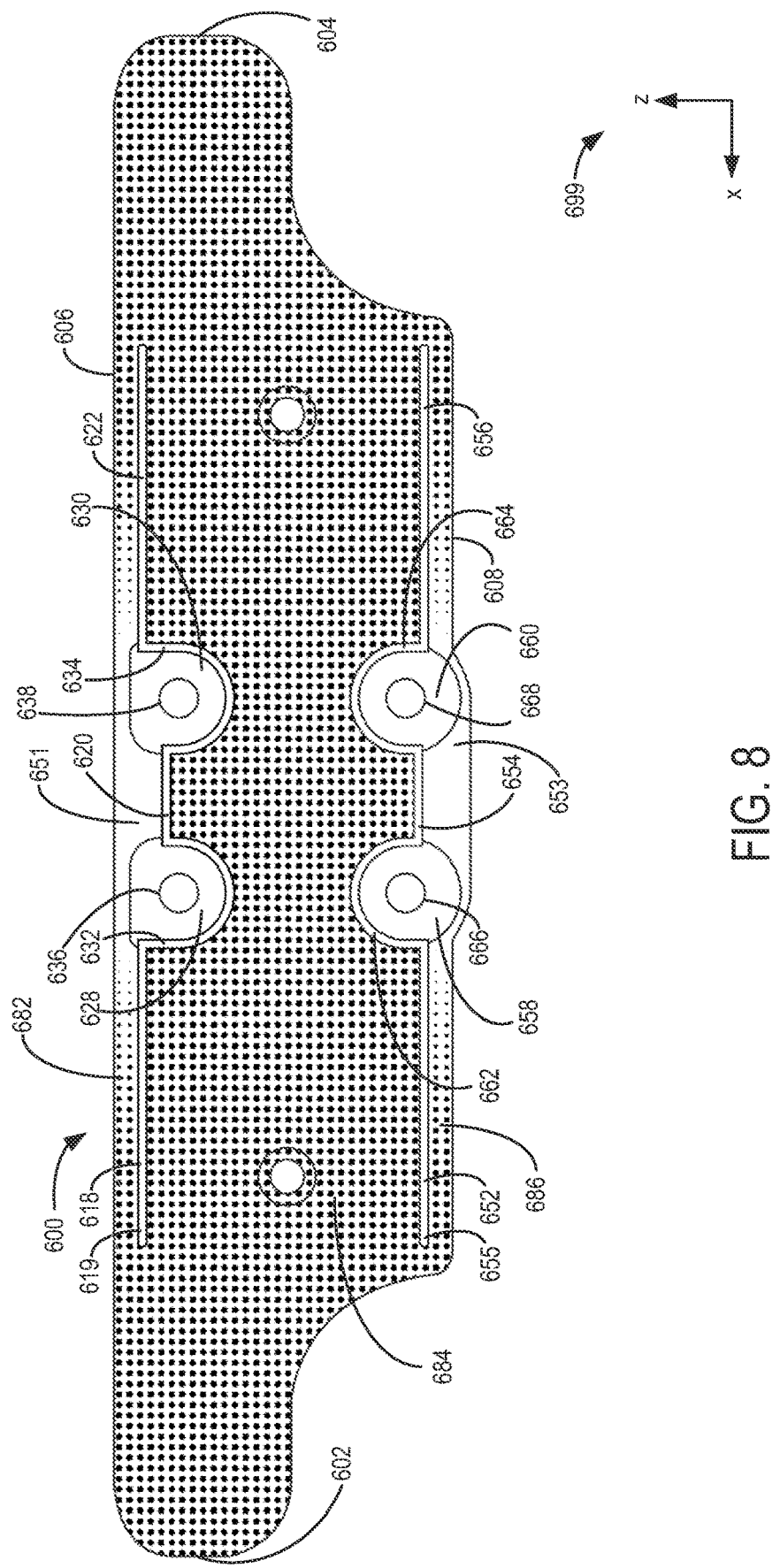
FIG. 8 shows the dynamic vibration absorber of FIGS. 6-7 with stipple shading indicating vibrational characteristics of portions of the dynamic vibration absorber.

The following description relates to various embodiments for medical imaging vibration reduction. A medical imaging system, such as the medical imaging system shown by FIG. 1, may include an x-ray radiation source configured to deliver x-ray radiation to an imaging area disposed within a bore of a gantry of the imaging system, as shown by FIG. 2. The imaging system includes a dynamic vibration absorber (DVA), such as the DVA shown by FIG. 3. The DVA is positioned proximate to the x-ray radiation source and is configured to reduce a vibration of the imaging system. Vibrational characteristics of the DVA may be adjusted (e.g., tuned) by replacing one or more mass-adjustment portions of the DVA (as shown by FIGS. 4-5 and FIG. 15) with different mass-adjustment portions having a different mass (as shown by FIG. 13), and/or replacing one or more biasing members spanning a clearance of the DVA (as shown by FIGS. 6-8, with an example clearance shown in cross-section by FIGS. 16-18) with different biasing members having a different stiffness (as shown by FIG. 13). By configuring the DVA to have adjustable vibrational characteristics (e.g., according to the method of FIG. 14), the DVA may reduce a vibration response of some portion of the imaging system due to vibration force created by the x-ray radiation source and/or other portions of the imaging system, as shown by FIGS. 9-12. In this way, noise resulting from operation of the imaging system may be reduced thereby increasing patient comfort and improving patient-operator communication. The decreased vibration of imaging system may additionally result in increased image quality and/or decreased wear of components of the imaging system.

The x-ray radiation source of the imaging system may be an x-ray tube configured to generate x-ray radiation. The x-ray tube may include a rotor configured to rotate within the x-ray tube to distribute heat created at the x-ray generation focal spot. For example, the focal spot may be continuously moved along the face of the rotor such that high rotor temperatures are not localized to a single point. This heat distribution may be utilized with higher rotational speeds in situations where higher amount and/or intensity of x-ray radiation is generated. Some imaging systems may include an x-ray tube configured for higher speeds (e.g., higher rotor rotational speeds) relative to x-ray tubes of other imaging systems. The spinning of the x-ray tube rotor may generate vibration of the imaging system. For example, the x-ray tube rotor may spin within the x-ray tube, which may result in vibration of the x-ray tube. In some examples described herein, the two terms "rotation" of the x-ray tube and "vibration" of the x-ray tube may be used synonymously to refer to the vibration generated by the spinning rotor of the x-ray tube. The vibration of the x-ray tube may result in vibration of other portions of the imaging system, such as the gantry. As a result, the vibrational characteristics of some imaging systems may be different relative to other imaging systems. For example, some x-ray tubes may vibrate at 145 Hz during operation, some x-ray tubes may vibrate at 160 Hz during operation, and some x-ray tubes may vibrate at 180 Hz during operation, with the higher vibrational frequencies corresponding to higher x-ray tube speeds.

In some imaging systems, the x-ray tube may vibrate at approximately a same frequency as a resonant frequency of the gantry structure during operation (e.g., 160 Hz), which may result in an undesirable forced vibration response. The resonance may increase an amount of noise produced by the imaging system and/or undesired movement of the gantry.

The speed of the x-ray tube may at least partially based on a rotational speed of the gantry. Because some gantries may rotate faster relative to other gantries, some x-ray tubes may be configured for higher speeds than other x-ray tubes. For example, an imaging system including a gantry having a slower, first rotational speed may also include an x-ray tube having a slower operating speed, and an imaging system including a gantry having a higher, second rotational speed may include an x-ray tube having a higher operating speed. However, in order to configure the x-ray tube to have the higher operating speed, the x-ray tube may have a different rotor geometry (e.g., a longer length) relative to x-ray tubes configured to have the lower operating speed. The altered geometry of the x-ray tube may change the vibrational characteristics of the x-ray tube (e.g., a vibrational amplitude of the x-ray tube) relative to the comparison x-ray tubes. As one example, some x-ray tubes configured for higher operating speeds may vibrate at a higher amplitude relative to x-ray tubes configured for lower operating speeds (e.g., 15 Hz higher, 20 Hz higher, etc.). The increased amplitude of the vibration may result in degradation of components of the imaging system (e.g., wear on bearings of the imaging system).

The speed of the x-ray tube may be selected in order to reduce undesired resonance of the vibration of the x-ray tube and the vibration of the gantry by purposely separating these two frequencies (e.g., vibration source frequency and gantry resonance frequency, respectively). As one example, the speed of the x-ray tube may be selected such that the x-ray tube has a peak vibration at 180 Hz, with the gantry having a peak vibration at 160 Hz. However, even with the x-ray tube and gantry having different peak vibrational frequencies, a significant forced response of the gantry structure may occur. For example, although the x-ray tube may be calibrated during manufacture to have certain vibrational characteristics (e.g., reduced vibration due to imbalance), some imbalance generated vibration may occur and/or increase over time. Additionally, because the x-ray tube speed is selected to be relatively high in order to vibrate at a different peak frequency relative to the gantry, imbalance of the x-ray tube may generate an undesirable amount of noise. The vibration of the x-ray tube may act on the supporting structure of the imaging system (e.g., the gantry) and may increase vibration of the gantry and/or noise produced by the gantry.

In order to reduce the vibration and noise of the x-ray tube and/or gantry, the DVA may be coupled to the imaging system at a location proximate to a source of the vibration. For example, the DVA may be coupled directly to the x-ray tube or proximate to the x-ray tube (e.g., coupled to a housing of the x-ray tube). The DVA is configured to vibrate out-of-phase relative to the x-ray tube and/or gantry with approximately a same amplitude of vibration in order to reduce a net vibration on the imaging system. In some examples, the DVA may be configured to vibrate at a same frequency as the gantry but out-of-phase relative to the gantry in order to reduce resonance between the x-ray tube and gantry. The DVA may be coupled to the imaging system such that the DVA automatically vibrates responsive to the vibration of the x-ray tube and/or gantry, without input by an operator of the imaging system.

The vibrational characteristics of the DVAs described herein may be adjusted (e.g., tuned) for use with various imaging systems, such as imaging systems that include an x-ray radiation source having different operating speeds and/or vibrational characteristics relative to x-ray radiation sources of other imaging systems, as described above. For example, the DVAs described herein may include a vibrational tuner that may affect the amount of movement of a sprung portion of the DVA (where the sprung portion is a mass or masses of the DVA that are configured to move relative to a stationary portion of the DVA and/or the component of the imaging system that the DVA is mounted to). The vibrational tuner may include replaceable biasing members and/or replaceable mass-adjustment portions that may be selected in order to adjust the vibrational frequency of the DVAs (e.g., the vibration frequency of a given DVA may be adjusted to be approximately the same as the vibrational frequency of the x-ray tube of the imaging system including the DVA). In this way, the vibrational frequency of the DVAs may be selected in order to reduce a larger amount of vibration of the x-ray tube and/or gantry.

In some examples, adjusting the vibrational characteristics of a DVA, such as the DVAs disclosed herein, may include coupling the DVA to the imaging system and measuring the vibrational characteristics (e.g., vibration frequency) of the x-ray tube during conditions in which the gantry is not rotated. Measuring the vibrational characteristics of the x-ray tube may include coupling a vibration measurement device (e.g., an accelerometer transducer) to the x-ray tube (e.g., directly to the x-ray tube, to a housing of the x-ray tube, or to a surface of the gantry proximate to the x-ray tube) and operating the x-ray tube at a same speed as an operating speed of the x-ray tube used while imaging a subject. The measurement device may measure the vibration characteristics of the x-ray tube during operation, such as vibration amplitude and frequency. If the vibrational characteristics are unsatisfactory (e.g., the vibration frequency is approximately the same as the vibration frequency of the gantry), the vibrational tuner may be adjusted, such as by replacing mass-adjustment portions of the DVA with different mass-adjustment portions (e.g., lighter or heavier mass-adjustment portions) and/or the replacing biasing members of the DVA with different biasing members (e.g., springs having higher or lower stiffness) in order to adjust the amount of vibration of the x-ray tube cancelled by the DVA.

Figure 1:
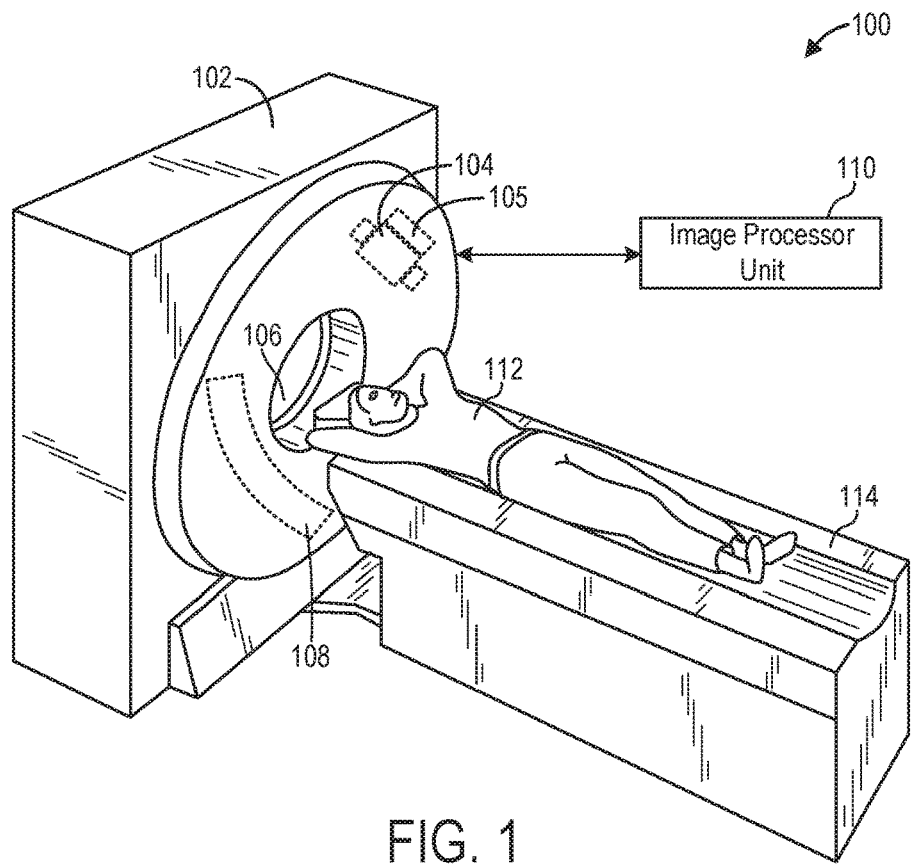
FIG. 1 shows a pictorial view of an imaging system including a dynamic vibration absorber, according to an embodiment.
Figure 2:
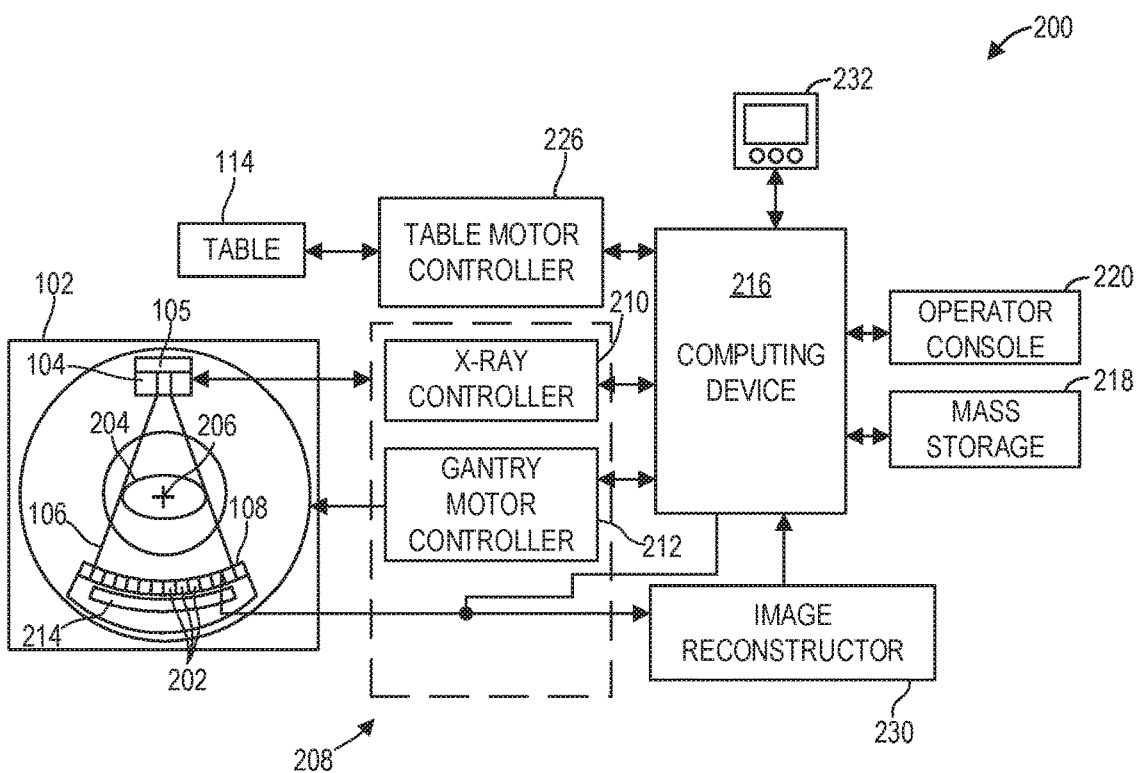
FIG. 2 shows a block schematic diagram of an exemplary imaging system including a dynamic vibration absorber, according to an embodiment.

Referring to FIG. 1, a perspective view of imaging system 100 is shown. Imaging system 100 is configured to image a subject 112 (e.g., a patient). In some examples, the subject may be an inanimate object, one or more manufactured parts, or foreign objects such as dental implants, stents, and/or contrast agents present within a body of a patient. The imaging system 100 includes a gantry 102, which in turn, may further include at least one x-ray radiation source 104 configured to project a beam of x-ray radiation 106 (see FIG. 2) for use in imaging the subject 112 laying on a table 114. Specifically, the x-ray radiation source 104 is configured to project the x-ray radiation beam 106 towards a detector array 108 positioned on the opposite side of the gantry 102. The imaging system 100 further includes a dynamic vibration absorber (DVA) 105 positioned proximate to the x-ray radiation source 104 within an interior of the imaging system 100 (as indicated by broken lines in FIG. 1). The DVA is configured to reduce an amount of vibration generated by operation of the x-ray radiation source 104, such as vibration resulting from rotation of a rotor of the x-ray radiation source 104. The DVA 105 may be similar to (e.g., the same as) the embodiments of the dynamic vibration absorbers described further below with reference to the other figures.

The imaging system 100 may further include an image processor unit 110 configured to reconstruct images of a target volume of the subject 112 acquired by projecting the x-ray radiation 106 through the subject 112 and receiving the attenuated x-rays at the detector array 108. In some known CT imaging system configurations, an x-ray radiation source (e.g., x-ray radiation source 104) projects a cone-shaped beam of x-ray radiation which is collimated to lie within a plane of a Cartesian coordinate system and generally referred to as an "imaging plane." The x-ray radiation beam passes through an object being imaged, such as the patient or subject 112. The x-ray radiation beam, after being attenuated by the object, impinges upon an array of x-ray radiation detectors (e.g., x-detector array 108). The intensity of the attenuated x-ray radiation beam received at the x-ray radiation detector array is dependent upon the attenuation of the x-ray radiation beam by the subject. Each detector element of the x-ray radiation detector array may produce a separate electrical signal that is a measurement of the x-ray radiation beam attenuation at the x-ray radiation detector location.

In some CT systems, the x-ray radiation source and the detector array are rotated with a gantry (e.g., gantry 102) within the imaging plane and around the object to be imaged (e.g., subject 112) such that an angle at which the x-ray radiation beam intersects the object constantly changes. A group of x-ray radiation attenuation measurements, e.g., projection data, from the detector array at one gantry angle is referred to as a "view." A "scan" of the object includes a set of views made at different gantry angles, or view angles, during one revolution of the x-ray radiation source and detector. It is contemplated that the embodiments described herein accrue to medical imaging modalities other than CT, so as used herein the term view is not limited to the use as described above with respect to projection data from one gantry angle. The term "view" is used to mean one data acquisition whenever there are multiple data acquisitions from different angles, whether from a CT/PET, X-ray (e.g. Vascular, Radiographic/Fluoroscopy, or Interventional Radiography), or SPECT acquisition, and/or any other modality including modalities yet to be developed as well as combinations thereof in fused embodiments.

To reduce the total scan time, a "helical" scan may be performed. To perform a "helical" scan, the patient is moved while the data for the prescribed number of slices is acquired. Such a system generates a single helix from a cone beam helical scan. The helix mapped out by the cone beam yields projection data from which images in each prescribed slice may be reconstructed.

As used herein, the phrase "reconstructing an image" is not intended to exclude conditions in which data representing an image is generated but a viewable image is not. Therefore, as used herein the term "image" broadly refers to both viewable images and data representing a viewable image.

FIG. 2 schematically shows an imaging system 200 similar to the imaging system 100 of FIG. 1. Imaging system 200 may include several components similar to those included by the imaging system 100, and similar components may be labeled similarly and not re-introduced (e.g., imaging system 200 includes dynamic vibration absorber 105, detector array 108, x-ray radiation source 104, etc.).

Detector array 108 includes a plurality of detector elements 202 that together sense the x-ray radiation 106 (e.g., similar to the example shown by FIG. 1) that pass through a subject 204 (e.g., a patient, similar to subject 112 shown by FIG. 1) to acquire corresponding projection data. In such a configuration, one or more rows of the detector elements 202 may be arranged in a parallel configuration for acquiring the projection data.

The imaging system 200 is configured to traverse different angular positions around the subject 204 for acquiring desired projection data. Accordingly, the gantry 102 and the components mounted thereon may be configured to rotate about a center of rotation 206 for acquiring the projection data, for example, at different energy levels. Alternatively, in embodiments where a projection angle relative to the subject 204 varies as a function of time, the mounted components may be configured to move along a general curve rather than along a segment of a circle.

As the x-ray radiation source 104 and the detector array 108 rotate, the detector array 108 collects data of the attenuated x-ray beams. In some examples, the individual detectors or detector elements 202 of the detector array 108 may comprise photon-counting detectors which register the interactions of individual photons.

In one embodiment, the imaging system 200 includes a control mechanism 208 to control movement of the components such as rotation of the gantry 102 and the operation of the x-ray radiation source 104. In certain embodiments, the control mechanism 208 further includes an x-ray controller 210 configured to provide power and timing signals to the x-ray radiation source 104. Additionally, the control mechanism 208 includes a gantry motor controller 212 configured to control a rotational speed and/or position of the gantry 102 based on imaging requirements.

In certain embodiments, the control mechanism 208 further includes a data acquisition system (DAS) 214 configured to sample analog data received from the detector elements 202 and convert the analog data to digital signals for subsequent processing. The data sampled and digitized by the DAS 214 is transmitted to a computer or computing device 216. In one example, the computing device 216 stores the data in a storage device 218. The storage device 218, for example, may include a hard disk drive, a floppy disk drive, a compact disk-read/write (CD-R/W) drive, a Digital Versatile Disc (DVD) drive, a flash drive, and/or a solid-state storage drive.

Additionally, the computing device 216 provides commands and parameters to one or more of the DAS 214, the x-ray controller 210, and the gantry motor controller 212 for controlling system operations such as data acquisition and/or processing. In certain embodiments, the computing device 216 controls system operations based on operator input. The computing device 216 receives the operator input, for example, including commands and/or scanning parameters via an operator console 220 operatively coupled to the computing device 216. The operator console 220 may include a keyboard (not shown) or a touchscreen to allow the operator to specify the commands and/or scanning parameters.

Although FIG. 2 illustrates only one operator console 220, more than one operator console may be coupled to the imaging system 200, for example, for inputting or outputting system parameters, requesting examinations, and/or viewing images. Further, in certain embodiments, the imaging system 200 may be coupled to multiple displays, printers, workstations, and/or similar devices located either locally or remotely, for example, within an institution or hospital, or in an entirely different location via one or more configurable wired and/or wireless networks such as the Internet and/or virtual private networks.

The computing device 216 uses the operator-supplied and/or system-defined commands and parameters to operate a table motor controller 226, which in turn, may control a table 114 which may comprise a motorized table. Particularly, the table motor controller 226 moves the table 114 for appropriately positioning the subject 204 in the gantry 102 for acquiring projection data corresponding to the target volume of the subject 204.

As previously noted, the DAS 214 samples and digitizes the projection data acquired by the detector elements 202. Subsequently, an image reconstructor 230 uses the sampled and digitized x-ray data to perform high-speed reconstruction. Although FIG. 2 illustrates the image reconstructor 230 as a separate entity, in certain embodiments, the image reconstructor 230 may form part of the computing device 216. Alternatively, the image reconstructor 230 may be absent from the imaging system 200 and instead the computing device 216 may perform one or more functions of the image reconstructor 230. Image reconstructor 230 may store the images reconstructed in the storage device 218 and/or transmit the reconstructed images to computing device 216 (e.g., display 232 of computing device 216) for generating useful patient information for diagnosis and evaluation. For example, display 232 of computing device 216 may allow the operator to evaluate the imaged anatomy. The display 232 may also allow the operator to select a volume of interest (VOI) and/or request patient information, for example, via a graphical user interface (GUI) for a subsequent scan or processing.

The various methods and processes described further herein may be stored as executable instructions in non-transitory memory on a computing device in imaging system 200. In one embodiment, image reconstructor 230 may include such executable instructions in non-transitory memory, and may apply the methods described herein to reconstruct an image from scanning data. In another embodiment, computing device 216 may include the instructions in non-transitory memory, and may apply the methods described herein, at least in part, to a reconstructed image after receiving the reconstructed image from image reconstructor 230. In yet another embodiment, the methods and processes described herein may be distributed across image reconstructor 230 and computing device 216.

Figure 3:
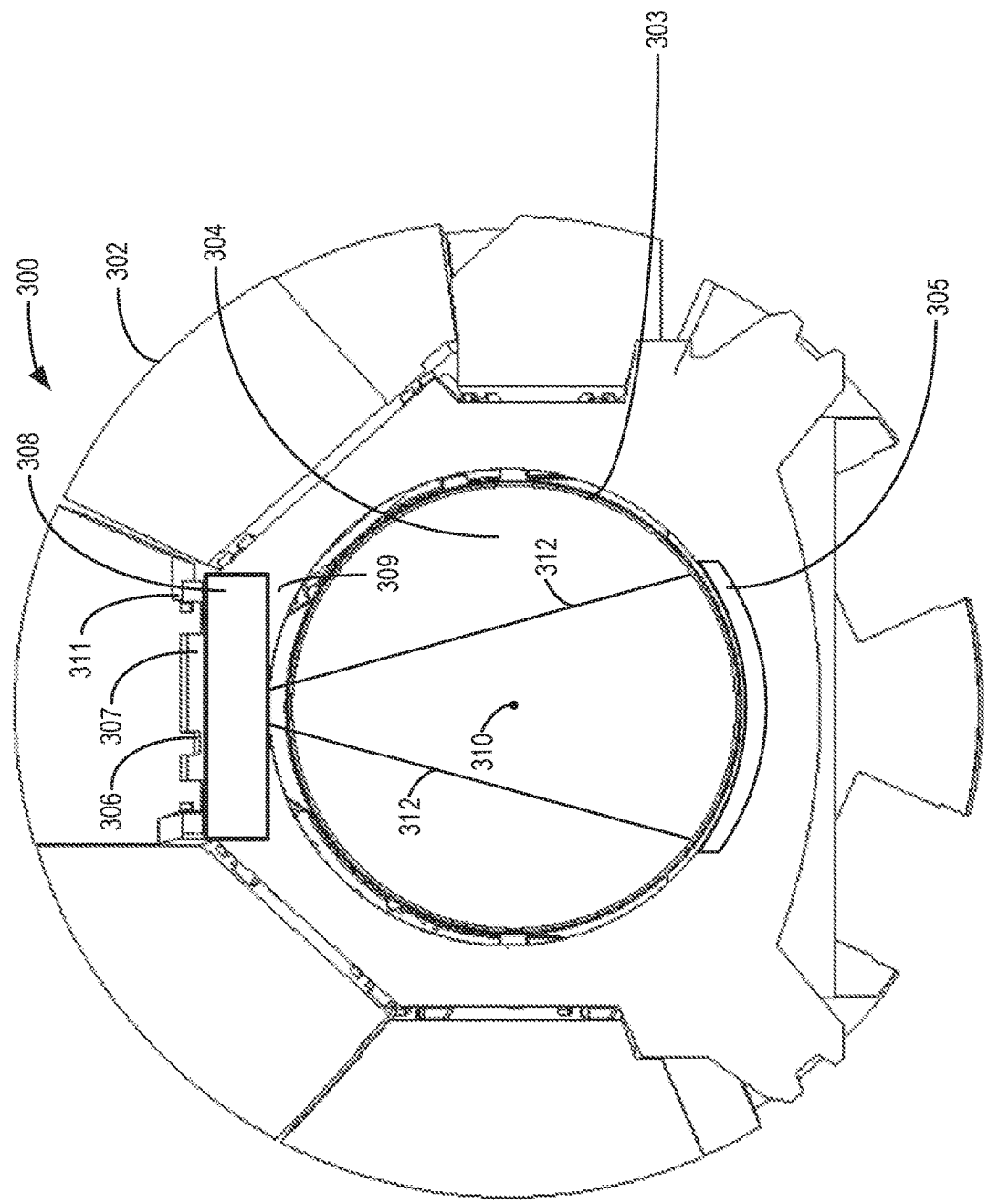
FIG. 3 shows an end view of an interior of an imaging system including a dynamic vibration absorber according to an embodiment.

Referring to FIG. 3, a view of an interior of an imaging system 300 is shown. Imaging system 300 may be similar to the imaging system 100 described above with reference to FIG. 1 and/or the imaging system 200 described above with reference to FIG. 2. Imaging system 300 includes a gantry 302, similar to gantry 102 described above with reference to FIGS. 1-2. Gantry 302 includes bore 303, where bore 303 is configured to receive a subject to be imaged by the imaging system 300 (e.g., a patient, similar to the example shown by FIG. 1). Similar to the examples described above, imaging system 300 includes x-ray radiation source 306 (e.g., an x-ray tube) configured to deliver x-ray radiation to imaging area 304 of the bore 303 of the gantry 302. For example, during conditions in which the subject is positioned within bore 303 for imaging, gantry 302 may rotate around central axis 310 in order to adjust a position of x-ray radiation source 306 (and x-ray beam 312 generated by the x-ray radiation source) relative to the subject. The x-ray radiation may intercepted by the subject and attenuated by the body of the subject, and the attenuated x-ray radiation may be received by a detector array 305 positioned opposite to the x-ray radiation source 306 across the central axis 310. The imaging system 300 may generate one or more views of the subject based on an output of the detector array 305, similar to the examples described above.

Imaging system 300 further includes dynamic vibration absorber (DVA) 308 arranged at the x-ray radiation source 306. In some examples, the DVA 308 may be coupled directly to the x-ray radiation source 306. For example, the x-ray radiation source 306 may be an x-ray tube configured to generate x-ray radiation, and the DVA 308 may be coupled directly to the x-ray tube. In other examples, the DVA 308 may be positioned adjacent to the x-ray radiation source 306 within the interior of the imaging system 300 but may not be directly coupled to the x-ray radiation source 306. For example, x-ray radiation source 306 may be mounted to a bracket or other mounting surface of the gantry 302 (e.g., mounting surface 311), and the DVA 308 may be mounted to a different bracket or mounting surface of the gantry 302 (e.g., mounting surface 309), proximate to (e.g., adjacent to) the x-ray radiation source 306. X-ray radiation source 306 may include a housing 307, with housing 307 enclosing the x-ray radiation source 306. In some examples, the housing 307 may be mounted to the gantry 302, and the DVA 308 may be mounted to the housing 307. X-ray radiation source 306 may be referred to herein as an x-ray tube, and housing 307 may be referred to herein as an x-ray tube housing.

DVA 308 may be configured to vibrate at approximately a same frequency as the x-ray radiation source 306 and/or gantry 302. However, DVA 308 may vibrate out-of-phase (e.g., 180 degrees out-of-phase) relative to the x-ray radiation source 306 and/or gantry 302, such that the vibration of the DVA 308 results in at least a partial cancellation of the vibration of the x-ray radiation source 306 and/or gantry 302. By cancelling at least part of the vibration of the x-ray radiation source 306 and/or gantry 302, an amount of noise generated by the imaging system 300 may be reduced and/or imaging quality may be increased. In order to configure the DVA 308 to vibrate at approximately the same frequency as the x-ray radiation source 306 and/or gantry 302, the DVA 308 may include components configured to be replaced with similar components having a different mass and/or stiffness. For example, the DVA 308 may include a plurality of mass-adjustment portions (e.g., plates), and one or more of the mass-adjustment portions may be replaced with respective different mass-adjustment portions having a different weight (e.g., heavier or lighter components) in order to increase or decrease the vibration frequency of the DVA 308. As another example, the DVA 308 may include one or more biasing members (e.g., springs), and one or more of the biasing members may be replaced with respective different biasing members having a different stiffness (e.g., a different spring constant). In some examples, the DVA 308 may include the mass-adjustment portions and the biasing members, such that adjustment of the vibration frequency of the DVA 308 may include replacement of one or more of the mass-adjustment portions, replacement of one or more of the biasing members, or both. Examples of DVAs similar to DVA 308 that include mass-adjustment portions and biasing members are described below with reference to FIGS. 4-8.

Referring collectively to FIGS. 4-5, a dynamic vibration absorber (DVA) 400 for an imaging system is shown. In some examples, DVA 400 may be included in the imaging systems described above (e.g., imaging system 100 shown by FIG. 1, imaging system 200 shown by FIG. 2, and/or imaging system 300 shown by FIG. 3). For example, DVA 308 shown by FIG. 3 and described above may be the same as the DVA 400 shown by FIGS. 4-5. FIG. 4 shows a perspective view of the DVA 400, and FIG. 5 shows an end view of the DVA 400. Reference axes 499 are included for comparison of the views shown.

DVA 400 includes a plurality of sections configured to set vibrational characteristics (e.g., a vibration frequency) of the DVA 400. For example, DVA 400 includes a first section 450, a second section 452, and a third section 454, where the first section 450 includes a first upper portion 402, a second upper portion 404, a third upper portion 406, a fourth upper portion 408, and a fifth upper portion 410 in a layered arrangement, the second section 452 includes a central portion 412, and the third section 454 includes a first lower portion 422 and a second lower portion 424 in a layered arrangement. The second section 452 is disposed between each of the first section 450 and third section 454 in a direction between an upper surface 451 and an opposing, lower surface 453 of the DVA 400 (e.g., the direction of the z-axis of reference axes 499, where the z-axis extends in a radial direction of a central axis of the imaging system, such as central axis 310 described above, during conditions in which the DVA 400 is coupled to the imaging system).

The DVA 400 may be coupled to the imaging system (e.g., coupled directly to an x-ray tube of the imaging system, or coupled proximate to the x-ray tube at a gantry of the imaging system) at the second section 452. The central portion 412 of second section 452 includes a first arm 414 having a first mount 418 (e.g., a first opening) and an opposing, second arm 416 having a second mount 420 (e.g., a second opening). The first mount 418 and second mount 420 may each be arranged in alignment with corresponding mounting surfaces of the x-ray tube, x-ray tube housing, or gantry, and respective fasteners (e.g., bolts) may be inserted through each of the first mount 418 and second mount 420 in order to secure (e.g., mount) the DVA 400 to the x-ray tube, x-ray tube housing, or gantry. The first arm 414 is separated (e.g., spaced apart) from the first section 450 by a first clearance 442, and the first arm 414 is separated from the third section 454 by an opposing, second clearance 444. The second arm 416 is separated from the first section 450 by a third clearance 446, and the second arm 416 is separated from the third section 454 by an opposing, fourth clearance 448.

In this configuration, the first arm 414 and second arm 416 may be maintained in position (e.g., remain stationary) relative to the surface to which the DVA 400 is mounted (e.g., the mounting surface of the x-ray tube, x-ray tube housing, or gantry), while the first section 450 and third section 454 may move (e.g., vibrate) relative to the first arm 414 and second arm 416. In this way, the first arm 414 and second arm 416 may act as respective biasing members of the DVA 400. In the example shown by FIGS. 4-5, the DVA 400 is in an unloaded condition (e.g., a condition in which vibrational load is not applied to the DVA 400 and the components of the DVA 400 are not vibrating). However, during conditions in which load (e.g., vibration) is applied to the DVA 400 such that the first section 450 and third section 454 move together relative to the first arm 414 and second arm 416 (e.g., in first direction 461, parallel to the direction of the z-axis of reference axes 499), the first arm 414 and second arm 416 apply a restoring force to the first section 450 and third section 454 that opposes the direction of motion of the first section 450 and third section 454 (e.g., the restoring force urges the first section 450 and third section 454 in second direction 463, opposite to the first direction 461). The first arm 414 and second arm 416 act to restore the DVA 400 to the condition shown by FIGS. 4-5 (e.g., the condition in which the first section 450 and third section 454 are not deformed or moved as a result of load applied to the DVA 400).

The components of the first section 450, second section 452, and third section 454 of the DVA 400 may be coupled together via respective fasteners (e.g., bolts) inserted through passage 434 and passage 436. The passage 434 extends through each portion of the DVA 400 along axis 426 from the upper surface 451 to the lower surface 453, and the passage 434 is opened at opening 430 arranged at the upper surface 451 and opening 438 arranged at the lower surface 453. Similarly, the passage 436 extends through each portion of the DVA 400 along axis 428 from the upper surface 451 to the lower surface 453, and the passage 436 is opened at opening 432 arranged at the upper surface 451 and opening 440 arranged at the lower surface 453. Coupling the first section 450, second section 452, and third section 454 together via fasteners disposed within the passage 434 and passage 436 as described above maintains a relative arrangement of the components of each section (e.g., maintains the second section 452 between the first section 450 and third section 454) and additionally increases an ease of removal of components of one or more of the sections, as described below.

Each section of the DVA 400 (e.g., first section 450, second section 452, and third section 454) contributes to the vibrational characteristics of the DVA 400. A mass of the DVA 400 resulting from the various sections may be selected in order to provide desired vibrational characteristics of the DVA 400. For example, the first upper portion 402, fifth upper portion 410, first lower portion 422, and second lower portion 424 may each have a mass greater than the second upper portion 404, third upper portion 406, and fourth upper portion 408. In some examples, the first upper portion 402, fifth upper portion 410, first lower portion 422, and second lower portion 424 may each have a mass of approximately 0.5 kilograms. The first upper portion 402, fifth upper portion 410, first lower portion 422, and second lower portion 424 may each be formed from a material having a higher density (e.g., steel), while the central portion 412 including first arm 414 and second arm 416 may be formed from a material having a lower density (e.g., aluminum). Further, each of the second upper portion 404, third upper portion 406, and fourth upper portion 408 may be formed from the first material having the higher density, but may have a lower thickness relative to each of the first upper portion 402, fifth upper portion 410, first lower portion 422, and second lower portion 424.

The DVA 400 may be configured such that a combined mass of the first upper portion 402, fifth upper portion 410, first lower portion 422, and second lower portion 424 causes the DVA 400 to vibrate at a frequency close to (e.g., within 10% of) a vibrational frequency of a component of the imaging system (e.g., the x-ray tube, x-ray tube housing, and/or gantry), and out-of-phase relative to the component, during conditions in which vibrational load is applied to the DVA 400. The selection of masses of the larger components of the DVA 400, such as the mass of the first upper portion 402, fifth upper portion 410, first lower portion 422, and second lower portion 424, may be referred to herein as a gross tuning of the DVA 400.

In order to further adjust the vibrational frequency of the DVA 400 to be approximately the same as the vibrational frequency of the component of the imaging system to which the DVA 400 is mounted (e.g., the x-ray tube, x-ray tube housing, or gantry), the DVA 400 includes the second upper portion 404, third upper portion 406, and fourth upper portion 408 each having a lesser mass relative to the first upper portion 402, fifth upper portion 410, first lower portion 422, and second lower portion 424. One or more of the second upper portion 404, third upper portion 406, and fourth upper portion 408 may be removed from the DVA 400 or replaced with a similar portion having a different mass (e.g., a higher mass or lower mass) in order to adjust the vibration frequency of the DVA 400.

Because each of the second upper portion 404, third upper portion 406, and fourth upper portion 408 has a smaller mass relative to each of the first upper portion 402, fifth upper portion 410, first lower portion 422, and second lower portion 424, removing or replacing one of the second upper portion 404, third upper portion 406, or fourth upper portion 408 results in a relatively small adjustment to the vibrational frequency of the DVA 400, whereas removing or replacing one of the first upper portion 402, fifth upper portion 410, first lower portion 422, or second lower portion 424 results in a relatively large adjustment to the vibrational frequency. Adjusting the vibrational frequency by removing or replacing one or more of the second upper portion 404, third upper portion 406, or fourth upper portion 408 as described above may be referred to herein as fine tuning of the DVA 400.

As one example of configuring the DVA 400 to reduce vibration of the imaging system, an operator of the imaging system (e.g., a technician) may couple the DVA 400 to the x-ray tube via the first mount 418 and second mount 420. The operator may couple a vibration measurement device (e.g., accelerometer transducer) to the x-ray tube and may configure the DVA 400 via gross tuning (e.g., removal or replacement of one or more of the first upper portion 402, fifth upper portion 410, first lower portion 422, and second lower portion 424) such that the vibration frequency of the DVA 400 is close to the vibration frequency of the x-ray tube (e.g., within 10% of the vibration frequency of the x-ray tube). The operator may then configure the DVA 400 via fine tuning (e.g., removal or replacement of one or more of the second upper portion 404, third upper portion 406, or fourth upper portion 408) in order to adjust the vibration frequency of the DVA 400 to be approximately the same as the vibration frequency of the x-ray tube (e.g., within 5% or less variation of the vibration frequency of the x-ray tube). In this configuration, during conditions in which the imaging system is operated for imaging of a subject, the DVA 400 vibrates with approximately the same frequency as the x-ray tube, with the vibration of the DVA 400 being out-of-phase (e.g., 180 degrees out-of-phase) relative to the vibration of the x-ray tube. As a result, a net vibration of the imaging system is reduced, which may reduce a noise produced by the imaging system and/or increase imaging quality (e.g., reduce image blur).

As described above, the DVA 400 may be positioned very close to (e.g., approximately at a same location as) the mounting locations of the x-ray tube. In this configuration, the portions of the DVA 400 positioned at the mounting locations move in a same in-phase relation (e.g., approximately zero phase shift) as the mounting portions of the x-ray tube. During conditions in which the DVA 400 is not coupled to the imaging system, the driving point transfer function for the force created by the x-ray tube has resonances that alternate with anti-resonances. Near the resonance frequencies, the displacement response of the x-ray tube relative to the forcing function (as the force changes from a lower frequency to a higher frequency) transitions from in-phase to out-of-phase between the force and the motion. Near the anti-resonance frequencies, the displacement response of the x-ray tube (as the force changes from a lower frequency to a higher frequency) transitions oppositely, from out-of-phase to in-phase. The anti-resonance frequency is the frequency at which the displacement response is very small despite the forcing function from the x-ray tube rotor having some significant input. Cancellation of the vibration may occur by shifting the anti-resonance at the x-ray tube mounting point to occur at approximately the same frequency as the rotor rotation speed by coupling the DVA 400 to the imaging system. For example, the DVA 400 may be tuned to have an appropriate resonance frequency (e.g., via gross tuning and fine tuning) and an appropriate mass such that the resonance of the DVA 400 alters the vibration characteristics of the gantry and shifts the anti-resonance frequency to occur at the rotating speed of the rotor, reducing a net vibration of the imaging system.

By coupling the DVA 400 to the imaging system proximate to the x-ray tube, an amplitude of the vibrations of the DVA 400 may more closely match an amplitude of the vibrations of the x-ray tube. For example, arranging the DVA 400 further from the x-ray tube may reduce an amount of vibrational load imparted to the DVA 400 by the x-ray tube. As a result, the amplitude of vibration of the DVA 400 may be reduced relative to the amplitude of vibration of the x-ray tube, and an amount of vibration cancellation provided by the DVA 400 (e.g., due to the vibration of the DVA 400 out-of-phase relative to the vibration of the x-ray tube) may be reduced. However, by coupling the DVA 400 to the imaging system proximate to the x-ray tube (e.g., directly to the x-ray tube or the x-ray tube housing), the amplitude of vibration of the DVA 400 may be increased, and noise reduction due to constructive interference of the vibration of the DVA 400 with the vibration of the x-ray tube may be increased.

Referring now collectively to FIGS. 6-8, another dynamic vibration absorber (DVA) 600 is shown. In particular, FIG. 6 shows a perspective view of the DVA 600, FIG. 7 shows a cross-sectional view of the DVA 600 along axis 690 shown by FIG. 6, and FIG. 8 shows an end view of the DVA 600 with stipple shading included to indicate portions of the DVA 600 that move responsive to a vibrational load applied to the DVA 600. DVA 600 may be included in an imaging system, such as the imaging system 100 shown by FIG. 1, imaging system 200 shown by FIG. 2, or imaging system 300 shown by FIG. 3 and described above. For example, DVA 308 described above with reference to FIG. 3 may be similar to (or the same as) DVA 600. Reference axes 699 are included in FIGS. 6-8 for comparison of the views shown.

DVA 600 includes a first section 692, a second section 694, and a third section 696. First section 692 includes upper portion 682, second section 694 includes central portion 684, and third section 696 includes lower portion 686. The upper portion 682, central portion 684, and lower portion 686 are in a layered arrangement such that the central portion 684 is disposed between the upper portion 682 and lower portion 686 in a direction between an upper surface 606 and an opposing, lower surface 608 of the DVA 600 (e.g., the direction of the z-axis of reference axes 699, where the z-axis extends in a radial direction of a central axis of the imaging system, such as central axis 310 described above, during conditions in which the DVA 600 is coupled to the imaging system).

In some examples, the first section 692, second section 694, and third section 696 of the DVA 600 may be formed together (e.g., cut, molded, etc.) from a single piece of material (e.g., steel, aluminum, etc.). For example, the DVA 600 may be formed via wire electrical discharge machining. Because the DVA 600 is configured to couple to the imaging system in a position offset from the central axis of the imaging system (e.g., configured to couple to the x-ray tube of the imaging system, similar to the position of the DVA 308 shown by FIG. 3 and described above), centrifugal force applied to the DVA 600 as a result of rotation of the gantry of the imaging system may be relatively high (e.g., up to 70 times a weight of the DVA 600). By forming the DVA 600 from a single piece of material, a durability of the DVA 600 may be increased and a weight of portions of the DVA 600 that are not configured to vibrate may be decreased.

The DVA 600 includes a first arm 651 and a second arm 653, with the first arm 651 including a first mount 628 disposed within recess 624 and a second mount 630 disposed within recess 626, and with the second arm 653 including a third mount 658 disposed within recess 670 and a fourth mount 660 disposed within recess 672. The first mount 628 includes a first opening 636, the second mount 630 includes a second opening 638, the third mount 658 includes a third opening 666, and the fourth mount 660 includes a fourth opening 668, with the first opening 636, second opening 638, third opening 666, and fourth opening 668 each configured to receive a respective fastener (e.g., bolt) for coupling the DVA 600 to the imaging system (e.g., coupling the DVA 600 to the x-ray tube, x-ray tube housing, or gantry). A first end 602 and an opposing, second end 604 of the DVA 600 may each be shaped (e.g., curved) such that the DVA 600 may mount in close proximity to other components of the imaging system (e.g., sensors and other devices) while still maintaining the ability of the DVA 600 to reduce vibrations of the x-ray tube, x-ray tube housing, and/or gantry. In some examples, the DVA 600 further includes a fifth mount 610 having a fifth opening 612 and a sixth mount 614 having a sixth opening 616, with the fifth opening 612 and sixth opening 616 each configured to receive respective fasteners. Each fastener coupled with the fifth opening 612 and sixth opening 616 may be positioned within the corresponding opening and separated from the corresponding opening by a clearance (e.g., a gap between outer surfaces of the fastener and inner surfaces of the opening). In this configuration, the fasteners may reinforce the coupled configuration of the DVA 600 with the gantry (e.g., provide support to couple the DVA 600 to the gantry in addition to fasteners inserted through the first opening 636, second opening 638, third opening 666, and fourth opening 668).

First arm 651 is separated (e.g., spaced apart) from the central portion 684 by a clearance 618 extending in a direction between the first end 602 and the second end 604 of the DVA 600. The clearance 618 includes a first portion 619 positioned toward the first end 602 and extends approximately parallel with upper surface 606 (e.g., in a direction parallel with the x-axis of reference axes 699), a second portion 632 positioned around the first mount 628 and following a curvature of the first mount 628, a third portion 620 extending between the first mount 628 and second mount 630 and parallel with the first portion 619, a fourth portion 634 positioned around the second mount 630 and following a curvature of the second mount 630, and a fifth portion 622 positioned toward the second end 604 and parallel with the first portion 619 and third portion 620. Each of the first portion 619, second portion 632, third portion 620, fourth portion 634, and fifth portion 622 are joined (e.g., not closed or separated by one or more walls, surfaces, etc.) such that the clearance 618 is a single, continuous opening (e.g., slot) extending through a thickness of the DVA 600 (e.g., in a direction of the y-axis of reference axes 699).

Second arm 653 is separated (e.g., spaced apart) from the central portion 684 by a clearance 652 extending in a direction between the first end 602 and the second end 604 of the DVA 600. The clearance 652 includes a first portion 655 positioned toward the first end 602 and extends approximately parallel with lower surface 608 (e.g., in a direction parallel with the x-axis of reference axes 699), a second portion 662 positioned around the third mount 658 and following a curvature of the third mount 658, a third portion 654 extending between the third mount 658 and fourth mount 660 and parallel with the first portion 655, a fourth portion 664 positioned around the fourth mount 660 and following a curvature of the fourth mount 660, and a fifth portion 656 positioned toward the second end 604 and parallel with the first portion 655 and third portion 654. Each of the first portion 655, second portion 662, third portion 654, fourth portion 664, and fifth portion 656 are joined (e.g., not closed or separated by one or more walls, surfaces, etc.) such that the clearance 652 is a single, continuous opening (e.g., slot) extending through a thickness of the DVA 600 (e.g., in a direction of the y-axis of reference axes 699).

In the configuration described above, during conditions in which the DVA 600 is coupled to the imaging system (e.g., coupled to the x-ray tube, x-ray tube housing, and/or gantry) via the first mount 628, second mount 630, third mount 658, and fourth mount 660, the first arm 651 and second arm 653 may remain approximately stationary relative to the mounting surface to which the DVA 600 is coupled, while the central portion 684 may move (e.g., vibrate) due to the separation of the central portion 684 from the first arm 651 by clearance 618 and due to the separation of the central portion 684 from the second arm 653 by clearance 652. Further, the DVA 600 may include one or more biasing members (e.g., springs) configured to apply a restoring force to the central portion 684 during conditions in which the central portion 684 is moved as a result of vibrational load applied to the DVA 600. The biasing members may urge the central portion 684 toward the position shown by FIGS. 6-8, where the central portion 684 is centered between the first arm 651 and second arm 653. In some examples, the clearance 618 and clearance 652 may each have a length of 2 millimeters in the direction from upper surface 606 to lower surface 608 (e.g., the direction of the z-axis of reference axes 699), and during conditions in which the central portion 684 moves due to vibrational load applied to the DVA 600, the central portion 564 may move 0.5 millimeters or less in the direction of the length of the clearance 618 and clearance 652 (e.g., the direction of the z-axis of reference axes 699).

The biasing members of the DVA 600 may be positioned within the third portion 620 of the clearance 618. In the configuration shown, the DVA 600 includes a recess 644 arranged at upper surface 606. A first passage 640 and a second passage 642 (shown by FIG. 7) extend from the central portion 684, through the first arm 651, and open at the recess 644. A first biasing member 678 (e.g., first spring) may be disposed within the first passage 640, and a second biasing member 680 (e.g., second spring) may be disposed within the second passage 642. The first biasing member 678 and second biasing member 680 may be maintained within the first passage 640 and second passage 642, respectively, by a cover 646 arranged within the recess 644 and coupled to the DVA 600 by a first fastener 648 and a second fastener 650 (e.g., bolts).

In order to adjust the vibrational characteristics of the DVA 600 (e.g., the vibration frequency of the DVA 600 responsive to vibration applied to the DVA 600 by the imaging system), one or more of the first biasing member 678 and second biasing member 680 may be removed or replaced. For example, first biasing member 678 may be replaced with a biasing member (e.g., a spring) having a different stiffness in order to adjust the vibrational characteristics of the DVA 600. Removing or replacing the first biasing member 678 and/or second biasing member 680 to adjust the vibrational characteristics of the DVA 600 may be referred to herein as fine tuning of the DVA 600. Larger adjustments to the vibrational characteristics of the DVA 600 (e.g., gross tuning of the DVA 600, similar to the gross tuning of DVA 400 described above) may be performed by adjusting the thickness (e.g., thickness in the direction of the z-axis of reference axes 699) of first arm 651, second arm 653, and/or central portion 684 (e.g., by removing material from first arm 651, second arm 653, and/or central portion 684, and/or widening the clearance 618 and/or clearance 652. For example, during manufacture of the DVA 600, the size of the clearance 618 and clearance 652 (e.g., the width of the clearance 618 and clearance 652 in the direction from the first end 602 to the second end 604, parallel to the x-axis of reference axes 699) may be selected based on predetermined vibrational characteristics of the imaging system to which the DVA 600 is coupled.

As one example, DVA 600 may be configured to reduce vibrations of imaging systems including an x-ray tube driven at relatively high speeds such that the x-ray tube vibrates with a frequency of 180 Hz. The thickness of the first arm 651, second arm 653, and/or central portion 684 and the size of clearance 618 and clearance 652 may be selected in order to gross tune the vibrational characteristics of the DVA 600 (e.g., adjust the vibrational characteristics by a larger, first amount) such that the DVA 600 vibrates with a frequency close to 180 Hz (e.g., within 10% of 180 Hz). Further, the stiffness of the first biasing member 678 and second biasing member 680 may be selected in order fine tune the vibrational characteristics of the DVA 600 (e.g., adjust the vibrational characteristics by a smaller, second amount) such that the DVA 600 responds vigorously (e.g., vibrates) at approximately 180 Hz. As such, the DVA 600 may counteract vibration (e.g., reduce the vibration) at the desired location on the imaging system during conditions in which the x-ray tube is operating at 180 Hz.

In order to illustrate motion of portions of the DVA 600 relative to each other during conditions in which vibrational load is applied to the DVA 600 (e.g., due to vibration of the surface to which the DVA 600 is coupled, such as the x-ray tube), FIG. 8 shows an end view of the DVA 600. The DVA 600 is shown with different size stipple shading at various portions of the DVA 600, where portions that are shaded with larger stippling may vibrate by a larger amount, and portions that are shaded with smaller stippling may vibrate by a smaller amount. Because the first mount 628, second mount 630, third mount 658, and fourth mount 660 are configured to fixedly mount to the mounting surface of the imaging system (e.g., the x-ray tube, x-ray tube housing, or gantry), the first mount 628, second mount 630, third mount 658, and fourth mount 660 are subject to a very small amount (or zero) vibration during conditions in which vibrational load is applied to the DVA 600. As such, the first mount 628, second mount 630, third mount 658, and fourth mount 660 are illustrated with no stippling. However, as described above, the central portion 684 may vibrate responsive to vibrational load applied to the DVA 600 (e.g., due to the first biasing member 678 and second biasing member 680 shown by FIG. 7, as well as the separation of the central portion 684 from the first arm 651 by clearance 618 and the separation of the central portion 684 from second arm 653 by clearance 652), and so the central portion 684 is illustrated with heavy stippling. Portions of the first arm 651 and portions of the second arm 653 positioned closer to the first end 602 and second end 604 may undergo larger amounts of vibration than portions positioned toward the mounts (e.g., first mount 628, second mount 630, third mount 658, and fourth mount 660), as indicated by the gradually increasing stippling size applied to the first arm 651 and second arm 653 in directions away from the mounts and toward the first end 602 and second end 604.

Similar to the examples described above, during conditions in which vibrational load is applied to the DVA 600 (e.g., force is applied to the DVA 600 as a result of vibration of other components of the imaging system, such as the x-ray tube), the DVA 600 is configured to vibrate at approximately a same frequency relative to the applied vibration but out-of-phase relative to the applied vibration. In some examples, the DVA 600 may vibrate 180 degrees out-of-phase relative to the vibration (e.g., vibrational load) applied to the DVA 600. In this configuration, the DVA 600 may cancel at least a portion of the vibrational load (e.g., lower the vibration response of the imaging system), such that a net vibration of the imaging system is reduced.

Although the DVA 400 shown by FIGS. 4-5 and the DVA shown by FIGS. 6-8 are described herein, in some embodiments a DVA (e.g., DVA 308 shown by FIG. 3) may include both removable and/or replaceable mass-adjustment portions (e.g., similar to second upper portion 404, third upper portion 406, fourth upper portion 408, etc. shown by FIG. 4 and described above) as well as removable and/or replaceable biasing members (e.g., first biasing member 678 and second biasing member 680 shown by FIG. 7 and described above).

Figure 9:
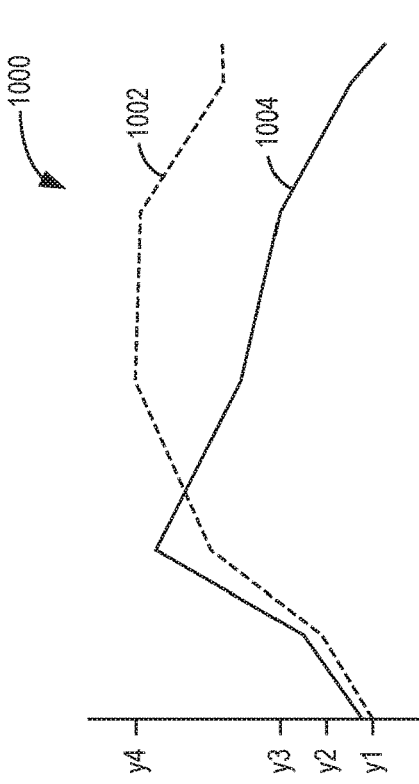
FIGS. 9-12 show graphs comparing vibration characteristics of an imaging system that does not include a dynamic vibration absorber to vibration characteristics of an imaging system that includes a dynamic vibration absorber.
Figure 11:
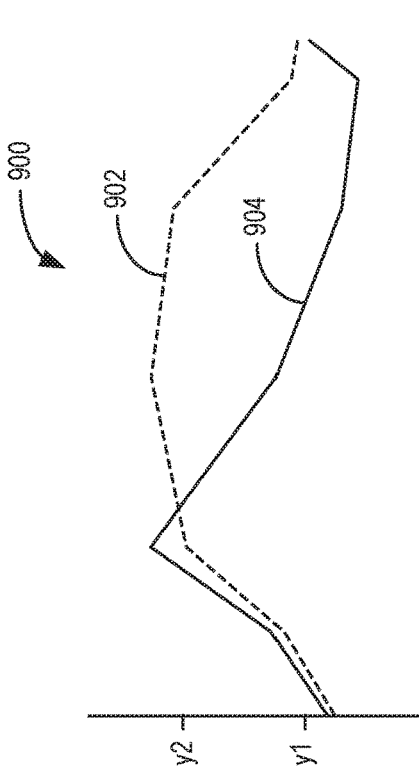
Figure 10:
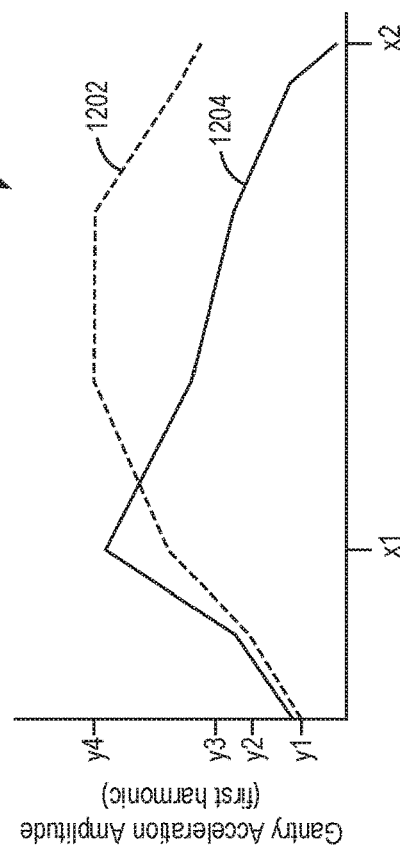
Figure 12:
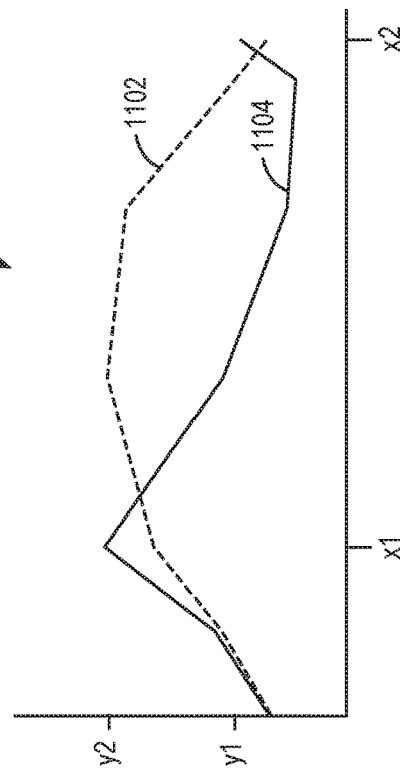
Figure 13:
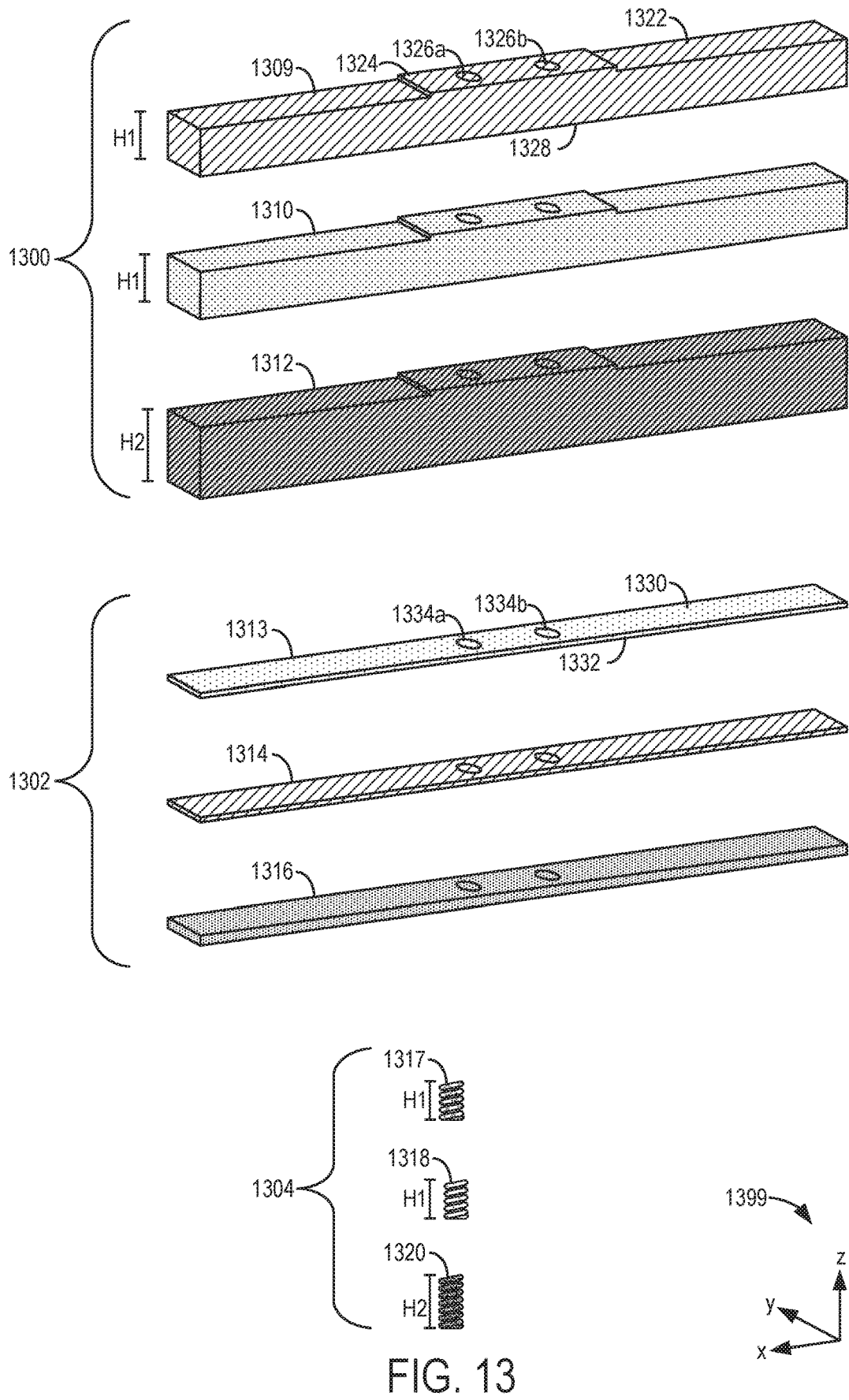
FIG. 13 shows different sets of mass-adjustment portions and biasing members, according to embodiments of the disclosure.

Referring to FIGS. 9-12, various graphs are shown illustrating vibrational characteristics of an x-ray radiation source and gantry of an imaging system for conditions in which a dynamic vibration absorber is coupled to the imaging system and conditions in which the dynamic vibration absorber is not coupled to the imaging system. In particular, FIG. 9 shows graph 900 illustrating x-ray radiation source overall acceleration amplitude (e.g., acceleration resulting from x-ray tube vibration) versus x-ray radiation source operating speed, FIG. 10 shows graph 1000 illustrating gantry overall acceleration amplitude (e.g., acceleration resulting from gantry vibration) versus x-ray radiation source operating speed, FIG. 11 shows graph 1100 illustrating x-ray radiation source acceleration amplitude for first harmonic vibration versus x-ray radiation source operating speed, and FIG. 12 shows graph 1200 illustrating gantry acceleration amplitude for first harmonic vibration versus x-ray radiation source operating speed. In the examples described with reference to FIGS. 9-12, the dynamic vibration absorber (DVA) may be any of the DVAs described above (e.g., DVA 308 shown by FIG. 3, DVA 400 shown by FIGS. 4-5, DVA 600 shown by FIGS. 6-8, etc.). The imaging system may be similar to (or the same as) imaging system 100 shown by FIG. 1, imaging system 200 shown by FIG. 2, and/or imaging system 300 shown by FIG. 3. The x-ray radiation source may be similar to the examples described above (e.g., x-ray radiation source 306 shown by FIG. 3, and/or x-ray radiation source 104 shown by FIGS. 1-2) and may be referred to herein as an x-ray tube. The gantry may be similar to the gantry 102 shown by FIGS. 1-2 and/or the gantry 302 shown by FIG. 3.

The graph 900 shown by FIG. 9 includes a plot 902 and a plot 904, with the plot 902 indicating x-ray radiation source acceleration amplitude versus x-ray radiation source operating speed during conditions in which the imaging system does not include the DVA, and with plot 904 indicating the same during conditions in which the imaging system includes the DVA (e.g., with the DVA coupled to the x-ray tube, a housing of the x-ray tube such as housing 307 shown by FIG. 3, or the gantry). The x-ray radiation source acceleration amplitude refers to acceleration of the x-ray radiation source resulting from vibration of the x-ray tube at various different frequencies including, but not limited to, a frequency of rotation of a rotor of the x-ray tube (e.g., the x-ray radiation source operating speed).

As shown by plot 902, acceleration of the x-ray radiation source may be relatively high for various x-ray radiation source operating speeds (e.g., within the range between x1 and x2, where x1 may correspond to 150 Hz in one example, and x2 may correspond to 180 Hz) during conditions in which the DVA is not coupled to the imaging system, where higher acceleration corresponds to higher vibration frequency. However, as shown by plot 904, coupling the DVA to the imaging system may significantly reduce the acceleration of the x-ray radiation source, which may significantly lower the vibration frequency of the x-ray radiation source. For example, for x-ray operating speeds between x1 and x2, the DVA may reduce acceleration of the x-ray radiation source from y2 (which may correspond to 1 m/s^2) to y1 (which may correspond to 0.5 m/s^2).

Further, as shown by graph 1000 of FIG. 10, the DVA may additionally decrease the gantry acceleration amplitude (e.g., acceleration resulting from vibration), resulting in decreased vibration of the gantry (e.g., a decreased frequency of vibration, decreased vibration amplitude, etc.). Plot 1002 shows gantry acceleration amplitude versus x-ray radiation source operating speed during conditions in which the imaging system does not include the DVA, and plot 1004 shows the same during conditions in which the imaging system includes the DVA (e.g., with the DVA coupled to the imaging system as described above). For example, for x-ray operating speeds between x1 and x2, the DVA may reduce the acceleration amplitude of the gantry attributed to vibration of the gantry from y4 (which may correspond to 3 m/s^2) to y3 (which may correspond to 1.5 m/s^2).

Although graph 900 and graph 1000 show acceleration of the x-ray radiation source and gantry, respectively, for various x-ray radiation source operating speeds, the acceleration amplitude shown by graph 900 and graph 1000 includes acceleration resulting from all vibration frequencies (e.g., a combination of harmonic frequencies). However, graph 1100 shown by FIG. 11 and graph 1200 shown by FIG. 12 show acceleration amplitudes resulting from only the first harmonic frequency (e.g., the frequency corresponding to the rotation speed of the rotor of the x-ray tube for a given x-ray radiation source operating speed). In particular, graph 1100 includes plot 1102 showing x-ray radiation source acceleration amplitude associated with the first harmonic versus x-ray radiation source operating speed during conditions in which the imaging system does not include the DVA, and plot 1104 shows the same during conditions in which the imaging system includes the DVA (e.g., with the DVA coupled to the imaging system as described above). Graph 1200 includes plot 1202 showing gantry acceleration amplitude associated with the first harmonic versus x-ray radiation source operating speed during conditions in which the imaging system does not include the DVA, and plot 1204 shows the same during conditions in which the imaging system includes the DVA (e.g., with the DVA coupled to the imaging system as described above). For both the x-ray radiation source and the gantry, the DVA substantially reduces acceleration resulting from first harmonic vibration. As a result, an amount of noise produced by the imaging system may be reduced, and a durability of components of the imaging system may be increased.

Referring to FIG. 13, various mass-adjustment portions and biasing members that may be included in the dynamic vibration absorbers (DVAs) described above are shown. The mass-adjustment portions and biasing members may be included as components of a set, in some examples. For example, a first set 1300 of mass-adjustment portions includes a first mass-adjustment portion 1309 (which may be the same as the second upper portion 404 described above with reference to FIGS. 4-5), a second mass-adjustment portion 1310, and a third mass-adjustment portion 1312. A second set 1302 of mass-adjustment portions includes a fourth mass-adjustment portion 1313 (which may be the same as the first lower portion 422 described above with reference to FIGS. 4-5), a fifth mass-adjustment portion 1314, and a sixth mass-adjustment portion 1316. A third set 1304 of biasing members includes a first biasing member 1317 (which may be the same as the first biasing member 678 of FIG. 7), a second biasing member 1318, and a third biasing member 1320.

Referring to the first set 1300, the first mass-adjustment portion 1309 includes a top surface 1322 and a bottom surface 1328, opposite the top surface. The top surface 1322 includes a raised portion 1324. The raised portion 1324 is configured to be in face-sharing contact with a bottom surface of a central portion of a second section of a DVA, such as central portion 412 of second section 452 of DVA 400. The raised portion 1324 may be raised above the remaining portions of the top surface 1322 by a suitable amount that provides clearance for movement of the fourth mass-adjustment portion 1313 relative to the second section of the DVA, as explained above with respect to FIG. 4. The raised portion 1324 further includes two through holes, a first through hole 1326a and a second through hole 1326b. When the first mass-adjustment portion 1309 is installed in a DVA (e.g., DVA 400), the through holes may each form a portion of a respective passage through which a respective fastener may be inserted in order to maintain the components of the DVA in position. The bottom surface 1328 may be configured to be in face-sharing contact with a top surface of another mass-adjustment portion, such as the second lower portion 424, when the first mass-adjustment portion 1309 is installed in a DVA.

The first mass-adjustment portion 1309 may have a length that extends along the x-axis (shown in the set of coordinates 1399), a width that extends along the y-axis, and a height that extends along the z-axis. The first mass-adjustment portion 1309 may be comprised of a high-density material such as steel and may have a first height, H1, that results in the first mass-adjustment portion having a first mass.

The set 1300 includes two additional mass-adjustment portions that have different masses than the first mass-adjustment portion, the second mass-adjustment portion 1310 and the third mass-adjustment portion 1312. Each of the second mass-adjustment portion 1310 and the third mass-adjustment portion 1312 may have a top surface, a raised portion of the top surface, two through holes, and a bottom surface, similar to the first mass-adjustment portion 1309. Further, the second mass-adjustment portion 1310 and the third mass-adjustment portion 1312 may each have the same length and width as the length and width of the first mass-adjustment portion 1309. The second mass-adjustment portion 1310 may have the same height (H1) as the first mass-adjustment portion 1309 while the third mass-adjustment portion 1312 may have a different height (H2). The height H2 of the third mass-adjustment portion 1312 may be larger than the height H1 of the first mass-adjustment portion 1309. The second mass-adjustment portion 1310 may be comprised of a lower density material than the first mass-adjustment portion 1309 (e.g., aluminum) and/or the second mass-adjustment portion 1310 may include internal voids, which may result in the second mass-adjustment portion 1310 having a lower mass than the first mass-adjustment portion 1309. The third mass-adjustment portion 1312 may be comprised of the same high-density material as the first mass-adjustment portion 1309, but due to the increased height of the third mass-adjustment portion 1312, the third mass-adjustment portion 1312 may have an increased mass relative to the first mass-adjustment portion.

In this way, the first set 1300 may include three different mass-adjustment portions each having a different mass. When tuning the vibration characteristics of a DVA, one of the mass-adjustment portions of the first set 1300 may be selected and installed in the DVA, which may provide desired vibration characteristics to match and counteract the vibration of the gantry to which the DVA is mounted.

While three mass-adjustment portions are shown in the first set 1300, the first set 1300 may include more or fewer mass-adjustment portions without departing from the scope of this disclosure. Further, each of the mass-adjustment portions in the first set 1300 may have the same dimensions, but may each have a different mass due to different material composition. In other examples, such as the example shown in FIG. 13, two or more of the mass-adjustment portions in the first set 1300 may have different dimensions (e.g., different heights) which may result in the mass-adjustment portions having different masses.

Referring next to the second set 1302, the fourth mass-adjustment portion 1313 includes a top surface 1330 and a bottom surface 1332, opposite the top surface. The top surface 1330 is configured to be in face-sharing contact with a bottom surface of a first upper portion of a first section of a DVA, such as first upper portion 402 of first section 450 of DVA 400. The top surface 1330 further includes two through holes, a first through hole 1334a and a second through hole 1334b. When the fourth mass-adjustment portion 1313 is installed in a DVA (e.g., DVA 400), the through holes may each form a portion of a respective passage through which a respective fastener may be inserted in order to maintain the components of the DVA in position. The bottom surface 1332 may be configured to be in face-sharing contact with a top surface of another mass-adjustment portion, such as the third upper portion 406, when the fourth mass-adjustment portion 1313 is installed in a DVA.

The fourth mass-adjustment portion 1313 may have a length that extends along the x-axis (shown in the set of coordinates 1399), a width that extends along the y-axis, and a height that extends along the z-axis. The fourth mass-adjustment portion 1313 may be comprised of a high-density material such as steel and may have a third height, smaller than the first height and the second height discussed above, that results in the fourth mass-adjustment portion having a third mass.

The second set 1302 includes two additional mass-adjustment portions that have different masses than the fourth mass-adjustment portion, the fifth mass-adjustment portion 1314 and the sixth mass-adjustment portion 1316. Each of the fifth mass-adjustment portion 1314 and the sixth mass-adjustment portion 1316 may have a top surface, two through holes, and a bottom surface, similar to the fourth mass-adjustment portion 1313. Further, the fifth mass-adjustment portion 1314 and the sixth mass-adjustment portion 1316 may each have the same length and width as the length and width of the fourth mass-adjustment portion 1313. The fifth mass-adjustment portion 1314 may have the same height as the fourth mass-adjustment portion 1313 while the sixth mass-adjustment portion 1316 may have a different height. The height of the sixth mass-adjustment portion 1316 may be larger than the height of the fourth mass-adjustment portion 1313. The fifth mass-adjustment portion 1314 may be comprised of a lower density material than the fourth mass-adjustment portion 1313 (e.g., aluminum) and/or the fifth mass-adjustment portion 1314 may include internal voids, which may result in the fifth mass-adjustment portion 1314 having a lower mass than the fourth mass-adjustment portion 1313. The sixth mass-adjustment portion 1316 may be comprised of the same high-density material as the fourth mass-adjustment portion 1313, but due to the increased height of the sixth mass-adjustment portion 1316, the sixth mass-adjustment portion 1316 may have an increased mass relative to the fourth mass-adjustment portion.

In this way, the second set 1302 may include three different mass-adjustment portions each having a different mass. When tuning the vibration characteristics of a DVA, one of the mass-adjustment portions of the second set 1302 may be selected and installed in the DVA, which may provide desired vibration characteristics to match and counteract the vibration of the gantry to which the DVA is mounted.

While three mass-adjustment portions are shown in the second set 1302, the second set 1302 may include more or fewer mass-adjustment portions without departing from the scope of this disclosure. Further, each of the mass-adjustment portions in the second set 1302 may have the same dimensions, but may each have a different mass due to different material composition. In other examples, such as the example shown in FIG. 13, two or more of the mass-adjustment portions in the second set 1302 may have different dimensions (e.g., different heights) which may result in the mass-adjustment portions having different masses.

Additionally, while the first set 1300 was described above as including mass-adjustment portions configured to include or replace second upper portion 404 and the second set 1302 was described above as including mass-adjustment portions configured to include or replace first lower portion 422, other mass-adjustment portions of DVA 400 described above may likewise be included as part of a set of replaceable mass-adjustment portions, where each mass-adjustment portion in a set of replaceable mass-adjustment portions has a different mass but is configured (e.g., due to dimensions, location of through holes, presence or absence of a raised portion, etc.) to be installed in the same position of a DVA.

Third set 1304 includes a plurality of biasing members, including the first biasing member 1317, the second biasing member 1318, and the third biasing member 1320, each configured to be installed in a DVA, such as DVA 600. The first biasing member 1317 may have a first height H1 that extends along the z-axis, and a length that extends along the x-axis and a width that extends along the y-axis. The first biasing member 1317 may be configured to be positioned in a passage of a DVA, such as first passage 640 of DVA 600, and may be configured to contact a cover of the DVA (e.g., cover 646) at a top portion of the biasing member and contact a bottom surface of a recess (e.g., recess 644) of the DVA at a bottom portion of the biasing member.

Likewise, the second biasing member 1318 and the third biasing member 1320 may each be configured to be positioned in a passage of a DVA, such as first passage 640 of DVA 600, and may be configured to contact a cover of the DVA (e.g., cover 646) at a top portion of the biasing member and contact a bottom surface of a recess (e.g., recess 644) of the DVA at a bottom portion of the biasing member. The second biasing member 1318 and the third biasing member 1320 may each have the same length and width as the first biasing member 1317. However, the second biasing member 1318 may have the same height H1 as the first biasing member 1317 while the third biasing member 1320 may have a different height H2, which may be higher than the first height H1. The first biasing member 1317 and the third biasing member 1320 may each be made of the same material(s) or may be made from material(s) having similar stiffness properties. The second biasing member 1318 may be made of a different material having different stiffness properties. As a result, each of the biasing members of third set 1304 may have a different stiffness/biasing characteristics when installed in a DVA.

In this way, the third set 1304 may include three different biasing members each having a different stiffness and/or biasing characteristic. When tuning the vibration characteristics of a DVA, one of the biasing members of the third set 1304 may be selected and installed in the DVA, which may provide desired vibration characteristics to match and counteract the vibration of the gantry to which the DVA is mounted.

While three biasing members are shown in the third set 1304, the third set 1304 may include more or fewer biasing members without departing from the scope of this disclosure. Further, each of the biasing members in the third set 1304 may have the same dimensions, but may each have a different stiffness due to different material composition. In other examples, such as the example shown in FIG. 13, two or more of the biasing members in the third set 1304 may have different dimensions (e.g., different heights) which may result in the biasing members having different biasing characteristics when installed in a DVA.

Additionally, while the third set 1304 was described above as including biasing members configured to include or replace first biasing member 1317, other biasing members of DVA 600 described above (e.g., second biasing member 680) may likewise be included as part of a set of biasing members, where each biasing member in a set of replaceable biasing members has a different stiffness and/or biasing characteristic but is configured (e.g., due to dimensions) to be installed in the same position of a DVA.

Figure 14:
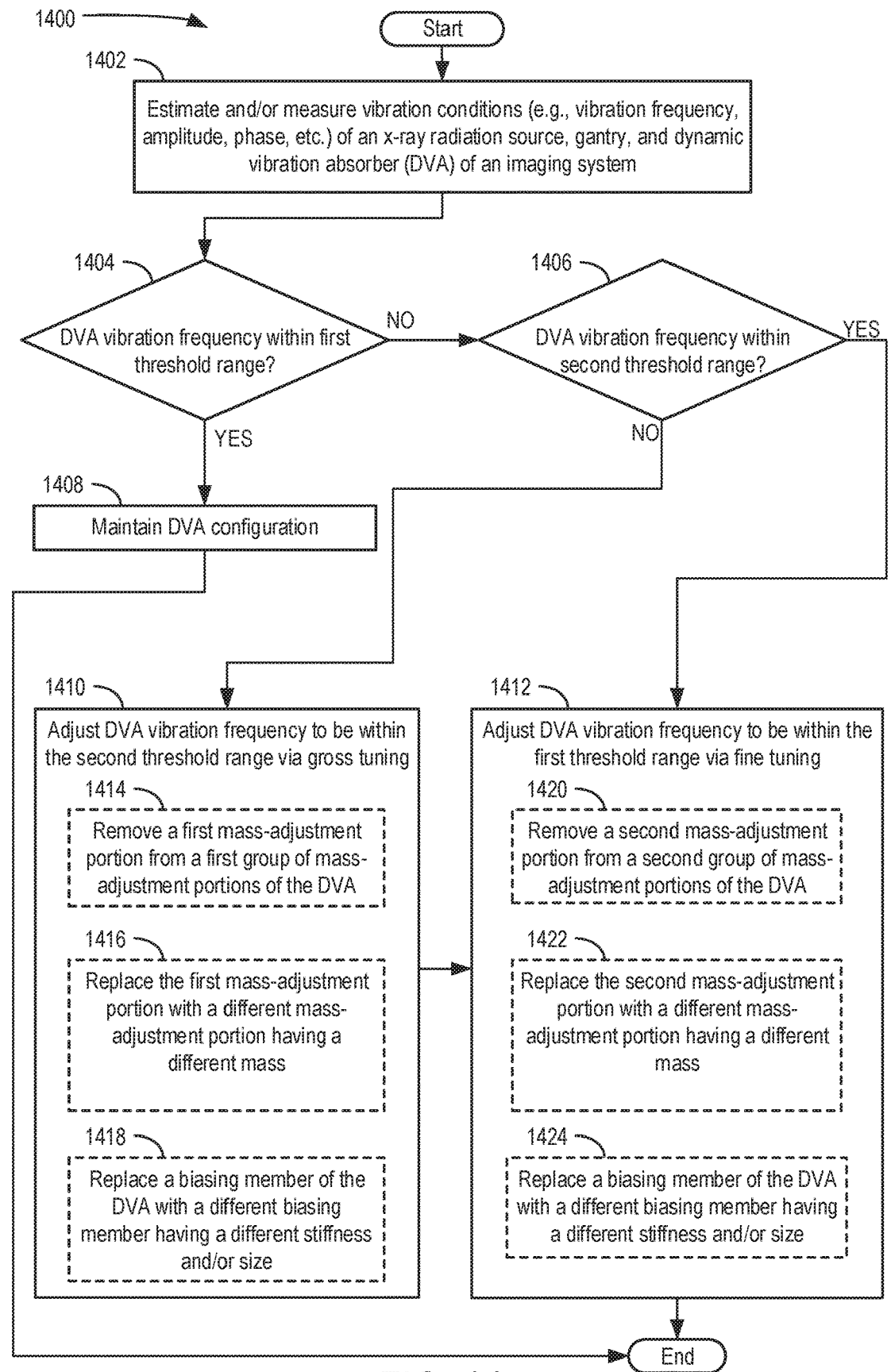
FIG. 14 is a flow chart illustrating a method for tuning a dynamic vibration absorber, according to an embodiment of the disclosure.

Referring to FIG. 14, a method 1400 for adjusting vibrational characteristics of a dynamic vibration absorber (DVA) is shown. In some examples, the DVA of method 1400 may be the DVA 400 shown by FIG. 4 and/or the DVA 600 shown by FIG. 6 and described above.

At 1402, vibration conditions of an x-ray radiation source and dynamic vibration absorber (DVA) of an imaging system are estimated and/or measured. The vibration conditions may include vibration frequency, vibration amplitude, vibration phase, etc. The vibration conditions may be determined by coupling an accelerometer to the DVA after the DVA has been mounted to (or near) the x-ray radiation source, as explained above. The DVA may be in a first configuration, which may include select replaceable mass-adjustment and/or biasing members being included in the DVA. While the gantry is maintained stationary, the rotor of the x-ray radiation source is rotated at a standard or target speed. The accelerometer may measure the vibration conditions during x-ray radiation source rotor rotation. The accelerometer may be operatively coupled to a computing device, which may in turn include or be operatively coupled to a display device. The vibration conditions (e.g., vibration frequency) may be determined based on the output from the accelerometer (e.g., by the computing device) and the determined vibration conditions may be displayed on the display device.

At 1404, method 400 includes determining if a vibration frequency of the DVA is within a first threshold range. The first threshold range may be a relatively small range around a target vibration frequency, such as +/−2 Hz around the target vibration frequency. The target vibration frequency may be +/−0.5 Hz. If the measured vibration frequency is within the first threshold range, method 1400 proceeds to 1408 to maintain the current DVA configuration. The current DVA configuration may sufficiently be reducing vibration of the x-ray radiation source, and thus tuning of the DVA is not indicated. Method 1400 then ends.

If the measured vibration frequency is not within the first threshold frequency, method 1400 proceeds to 1406 to determine if the vibration frequency of the DVA is within a second threshold range. The second threshold range may be a range around the target frequency that is greater than the first range, such as within +/−10 Hz of the target frequency. If the vibration frequency is not within the second threshold range, method 1400 proceeds to 1410 to adjust the DVA vibration frequency to be within the second threshold range via gross tuning. Adjusting the DVA vibration frequency to be within the second threshold range via gross tuning may include removing a first mass-adjustment portion of the DVA, as indicated at 1414. The first mass-adjustment portion may be from a first group of mass-adjustment portions that have a larger mass than other mass-adjustment portions of the DVA. For example, the first mass-adjustment portion may be the first lower portion 422 or the second lower portion 424 of DVA 400.

Adjusting the DVA vibration frequency to be within the second threshold range via gross tuning may further include replacing the first lower portion (e.g., first mass-adjustment portion) with a different mass-adjustment portion having a different mass, as indicated at 1416. For example, if the first lower portion 422 is removed, the first lower portion 422 may be replaced with second mass-adjustment portion 1310 or third mass-adjustment portion 1312, each of which have a different mass than the first lower portion 422. The decision of which mass-adjustment portion should replace the first mass-adjustment portion (e.g., whether the replacement mass-adjustment portion has a higher mass or a lower mass than the first mass-adjustment portion) may be based on the vibration frequency of the DVA, e.g., whether the vibration frequency is greater than or less than the target frequency and/or the magnitude of the difference between the target frequency and the measured vibration frequency of the DVA.

In some examples, adjusting the DVA vibration frequency to be within the second threshold range via gross tuning may include replacing a biasing member of the DVA with a different biasing member having a different stiffness and/or size, as indicated 1418. For example, a first biasing member (e.g., biasing member 678) currently installed in the DVA may be removed and replaced with a different biasing member (e.g., second biasing member 1318 or third biasing member 1320). In some examples, both the first mass-adjustment portion and the biasing member may be replaced. In other examples, only the first mass-adjustment portion or only the biasing member may be replaced. In still further examples, the first mass-adjustment portion may be removed but not replaced, and instead the DVA may be gross tuned by completely eliminating that mass-adjustment portion from the DVA.

Returning to 1406, if the vibration frequency of the DVA is within the second threshold range, method 1400 proceeds to 1412 to adjust the DVA vibration frequency to be within the first threshold range via fine-tuning. In some examples, after adjusting the DVA vibration frequency to be within the second threshold range via gross tuning, as performed at 1410, method 1400 may also proceed to 1412 to fine-tune the vibration frequency of the DVA. For example, after gross-tuning the DVA at 1410, the vibration of the DVA may again be measured by rotating the rotor of the x-ray radiation source and if the vibration frequency is not within the first threshold range, the method may proceed to 1412.

Adjusting the DVA vibration frequency to be within the first threshold range via fine-tuning may include removing a second mass-adjustment portion of the DVA, as indicated at 1420. The second mass-adjustment portion may be from a second group of mass-adjustment portions that have a smaller mass than other mass-adjustment portions of the DVA. For example, the second mass-adjustment portion may be the second upper portion 404 of DVA 400.

Adjusting the DVA vibration frequency to be within the first threshold range via fine tuning may further include replacing the second mass-adjustment portion with a different mass-adjustment portion having a different mass, as indicated at 1422. For example, if the second upper portion 404 is removed, the second upper portion 404 may be replaced with fifth mass-adjustment portion 1314 or sixth mass-adjustment portion 1316, each of which have a different mass than the second upper portion 404. The decision of which mass-adjustment portion should replace the second mass-adjustment portion (e.g., whether the replacement mass-adjustment portion has a higher mass or a lower mass than the second mass-adjustment portion) may be based on the vibration frequency of the DVA, e.g., whether the vibration frequency is greater than or less than the target frequency and/or the magnitude of the difference between the target frequency and the measured vibration frequency of the DVA.

In some examples, adjusting the DVA vibration frequency to be within the first threshold range via fine tuning may include replacing a biasing member of the DVA with a different biasing member having a different stiffness and/or size, as indicated 1424. For example, a first biasing member (e.g., biasing member 678) currently installed in the DVA may be removed and replaced with a different biasing member (e.g., second biasing member 1318 or third biasing member 1320). In some examples, both the second mass-adjustment portion and the biasing member may be replaced. In other examples, only the second mass-adjustment portion or only the biasing member may be replaced. In still further examples, the second mass-adjustment portion may be removed but not replaced, and instead the DVA may be fine-tuned by completely eliminating that mass-adjustment portion from the DVA. Method 1400 then ends.

While not shown in FIG. 14, it should be appreciated that at least in some examples, after replacing a mass-adjustment portion and/or biasing member of a DVA, the vibration condition of the DVA may be measured, and the process of replacing mass-adjustment portions and/or biasing members may be repeated until the vibration frequency is within the first threshold range. Further, while the tuning process described herein is performed while the gantry is stationary, in some examples, the gantry may be rotated during the tuning process. Further still, rather than relying on an external accelerometer that has to be coupled to the DVA and then removed, the vibration condition may be determined based on output from one or more balance sensors present on the imaging system.

Referring to FIG. 15, a cross-sectional view of the DVA 400 of FIGS. 4-5 is shown. FIG. 15 shows DVA 400 coupled to a mounting surface 1500 (e.g., a housing of an x-ray tube of an imaging system including a gantry, such as housing 307 enclosing the x-ray radiation source 306 described above with reference to FIG. 3). DVA 400 is coupled (e.g., mounted) to the mounting surface 1500 via fastener 1502 (e.g., a bolt) inserted through each of first mount 418 and mounting surface opening 1510. In some examples, fastener 1502 may include threads configured to engage with counterpart threads of first mount 418 and/or mounting surface opening 1510 in order to maintain the DVA 400 in the coupled configuration with mounting surface 1500. A head 1503 of the fastener 1502 may be spaced apart from the first arm 414 by a first spacer 1504 (e.g., a first washer), and the first arm 414 of the DVA 400 may be spaced apart from the mounting surface 1500 by a second spacer 1506 (e.g., a second washer). As a result, a clearance 1508 is formed between the DVA 400 and the mounting surface 1500, with the DVA 400 coupled to the mounting surface 1500 only at the first mount 418 and the second mount 420 (shown by FIGS. 4-5). Fastener 1502 compresses the first spacer 1504, first arm 414, second spacer 1506, and mounting surface 1500 together at the location of the first mount 418 and mounting surface opening 1510 in order to couple the DVA 400 to the mounting surface 1500.

By providing the clearance 1508 between the DVA 400 and the mounting surface 1500 via the second spacer 1506, the DVA 400 is maintained in the coupled configuration with the mounting surface 1500 while portions of the DVA 400 may move (e.g., vibrate) relative to the mounting surface 1500. For example, during conditions in which vibrational load is applied to the DVA 400 (e.g., conditions in which the x-ray tube is energized and a motion of the rotor of the x-ray tube vibrates the mounting surface 1500), the portion of the first arm 414 coupled to the mounting surface 1500 at the first mount 418 may be maintained in position relative to the mounting surface 1500, and portions of the DVA 400 positioned away from the first arm 414 (e.g., first upper portion 402, second upper portion 404, third upper portion 406, fourth upper portion 408, fifth upper portion 410, first lower portion 422, and second lower portion 424) may vibrate out-of-phase relative to the mounting surface 1500 (e.g., similar to the examples described above). The out-of-phase motion of the portions of the DVA 400 relative to the mounting surface 1500 may reduce a net vibrational effect of the x-ray tube on the imaging system to which the x-ray tube is mounted (e.g., imaging system 300 described above with reference to FIG. 3).

Referring collectively to FIGS. 16-18, different cross-sectional views of a DVA 1601 are shown. DVA 1601 is shown coupled (e.g., mounted) to mounting surface 1600, which may be similar to mounting surface 1500 described above with reference to FIG. 15. DVA 1601 may be similar to DVA 600 described above with reference to FIGS. 6-8. For example, DVA 600 includes first arm 1602, second arm 1606, central portion 1604, mount 1622, clearance 1612, and clearance 1614, which may be similar to first arm 651, second arm 653, central portion 684, fifth mount 610, clearance 618, and clearance 652, respectively, of DVA 600. DVA 1601 includes opening 1617 and opening 1619 each adapted to receive a respective fastener (e.g., bolt) to couple the DVA 1601 to the mounting surface 1600. FIG. 16 shows DVA 1601 coupled to mounting surface 1600 by fastener 1608 inserted through opening 1617 and fastener 1610 inserted through opening 1619. Fastener 1608 is further inserted through opening 1621 of mounting surface 1600, and fastener 1610 is further inserted through opening 1623 of mounting surface 1600. In this configuration, the DVA 1601 is maintained coupled to the mounting surface 1600 by each of fastener 1608 and fastener 1610. DVA 1601 may include additional openings (e.g., similar to second opening 638 and fourth opening 668 shown by FIGS. 6-8) adapted to receive fasteners to further couple the first arm 1602 and second arm 1606 of the DVA 1601 to the mounting surface 1600.

DVA 1601 is configured such that the first arm 1602 and second arm 1606 are positioned in direct, face-sharing contact with the mounting surface 1600 at the location where the fastener 1608 sits within opening 1617 and opening 1621, and the location where fastener 1610 sits within opening 1619 and opening 1623. For example, first arm 1602 forms interface 1616 with mounting surface 1600 at the opening 1617, and second arm 1606 forms interface 1618 with mounting surface 1600 at the opening 1618, where the interface 1616 and interface 1618 do not include gaps or clearances between the DVA 1601 and the mounting surface 1600. Further, the first arm 1602 and second arm 1606 may be positioned in direct, face-sharing contact with the mounting surface 1600 at the additional openings similar to second opening 638 and fourth opening 668 shown by FIGS. 6-8.

However, other portions of the DVA 1601 are configured to be spaced apart from the mounting surface 1600 such that the portions of the DVA 1601 not directly coupled to the mounting surface 1600 may move relative to the mounting surface 1600 during conditions in which vibrational load is applied to the DVA 1601 (e.g., similar to the examples described above). For example, as vibrational load is applied to DVA 1601 due to vibration of the mounting surface 1600, portions of the DVA 1601 positioned in face-sharing contact with the mounting surface 1600 may not move relative to the mounting surface 1600, while portions of the DVA 1601 arranged further away from the opening 1617 and opening 1619 (e.g., central portion 1604 arranged between clearance 1612 and clearance 1614, with between clearance 1612 and clearance 1614 separating the central portion 1604 from the opening 1617 and opening 1619) may vibrate out-of-phase relative to the mounting surface 1600 (e.g., similar to the example described above with reference to FIG. 8). In particular, clearance 1620 (shown in FIG. 16, and in the enlarged views of inset 1624 of FIG. 17 and inset 1626 of FIG. 18) is arranged between at least the central portion 1604 and the mounting surface 1620, with the clearance 1620 separating (e.g., spacing apart) the central portion 1604 from the mounting surface 1620. Clearance 1620 may additionally extend between the DVA 1601 and the mounting surface 1600 to separate other portions of the DVA 1601 from the mounting surface 1600, such as portions not forming interface 1616 and interface 1618 (e.g., the portions arranged away from opening 1617 and opening 1619, as shown by FIGS. 17-18). The out-of-phase motion of the portions of the DVA 1601 relative to the mounting surface 1500 may reduce a net vibrational effect of the x-ray tube on the imaging system to which the x-ray tube is mounted (e.g., imaging system 300 described above with reference to FIG. 3).

The technical effect of coupling the DVA to the imaging system and configuring the DVA to vibrate at approximately a same frequency as, but out-of-phase relative to, components of the imaging system is to reduce noise produced by the imaging system (e.g., within the imaging area of the imaging system) and increase a reliability of components of the imaging system (e.g., reduce a likelihood of wear of the components resulting from vibration, such as the x-ray tube). The DVA may reduce the vibration of the imaging system without increasing the size and/or stiffness of the gantry, which may reduce a cost and/or amount of space occupied by the imaging system.

In one embodiment, a dynamic vibration absorber (DVA) for an imaging system, comprising: a mount portion including one or more apertures and adapted to fixedly couple to a mount surface within the imaging system; a sprung portion; and a vibrational tuner, where when the mount portion is mounted to the mount surface and during operation of the imaging system, the sprung portion moves relative to the mount surface, an amount of movement of the sprung portion based at least in part on the vibrational tuner. In a first example of the DVA, during operation of the imaging system, the vibrational tuner causes the sprung portion to exhibit one or more vibrational characteristics that match one or more vibrational characteristics of the imaging system. A second example of the DVA optionally includes the first example, and further includes wherein the vibrational tuner causes the sprung portion to exhibit a vibrational frequency within a threshold range of a vibrational frequency of the imaging system. A third example of the DVA optionally includes one or both of the first and second examples, and further includes wherein the vibrational tuner causes the sprung portion to exhibit a vibrational phase that is out-of-phase of a vibrational phase of the imaging system. A fourth example of the DVA optionally includes one or more or each of the first through third examples, and further includes wherein the vibrational tuner is a first vibrational tuner selected from among a plurality of first vibrational tuners, each first vibrational tuner having a different mass. A fifth example of the DVA optionally includes one or more or each of the first through fourth examples, and further includes wherein each first vibrational tuner has a mass within a smaller, first range. A sixth example of the DVA optionally includes one or more or each of the first through fifth examples, and further includes a second vibrational tuner selected from among a plurality of second vibrational tuners, each second vibrational tuner having a mass within a larger, second range. A seventh example of the DVA optionally includes one or more or each of the first through sixth examples, and further includes wherein the vibrational tuner is coupled between the mount portion and the sprung portion and is configured to bias the sprung portion relative to the mount portion. An eighth example of the DVA optionally includes one or more or each of the first through seventh examples, and further includes wherein the vibrational tuner comprises a biasing member selected from among a plurality of biasing members, where at least two biasing members of the plurality of biasing members have a different stiffness relative to each other. A ninth example of the DVA optionally includes one or more or each of the first through eighth examples, and further includes wherein the mount portion includes a first arm and an opposing, second arm, the first and second arms each having an aperture adapted to receive a respective fastener.

In one embodiment, a method comprises: coupling a dynamic vibration absorber (DVA) to a mount surface of an imaging system; determining a vibration frequency of the DVA while rotating a rotor of the imaging system; and fine-tuning the vibration frequency of the DVA based on the determined vibration frequency. In a first example of the method, the DVA includes a plurality of mass-adjustment portions, and wherein fine-tuning the vibration frequency includes removing, replacing, or adding one or more of the plurality of mass-adjustment portions to or from the DVA. A second example of the method optionally includes the first example, and further includes wherein fine-tuning the vibration frequency by removing, replacing, or adding one or more of the plurality of mass-adjustment portions comprises fine-tuning the vibration frequency by removing, replacing, or adding a first, lower mass mass-adjustment portion. A third example of the method optionally includes one or both of the first and second examples, and further includes gross-tuning the vibration frequency by removing, replacing, or adding a second, higher mass mass-adjustment portion to or from the DVA. A fourth example of the method optionally includes one or more or each of the first through third examples, and further includes wherein the DVA includes one or more biasing members, and wherein fine-tuning the vibration frequency includes replacing a biasing member of the one or more biasing members the DVA with a biasing member having a different stiffness.

In one embodiment, a system comprises: a gantry; an x-ray radiation source coupled to the gantry and including an x-ray tube and a housing; and a dynamic vibration absorber (DVA) configured to couple to one of the gantry, the x-ray tube, or the housing, the DVA comprising a mount portion, a sprung portion, and one or more interchangeable elements configured to adjust vibration characteristics of the DVA. In a first example of the system, the one or more interchangeable elements include one or more mass-adjustment portions. A second example of the system optionally includes the first example, and further includes wherein the one or more interchangeable elements include one or more biasing members. A third example of the system optionally includes one or both of the first and second examples, and further includes wherein the mount portion and the sprung portion are formed as a unitary piece. A fourth example of the system optionally includes one or more or each of the first through third examples, and further includes wherein the DVA is configured to vibrate out-of-phase relative a vibration of the x-ray tube.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A dynamic vibration absorber (DVA) for an imaging system, comprising:
   a mount portion including one or more apertures and adapted to fixedly couple to a mount surface within the imaging system;
   a sprung portion; and
   a vibrational tuner, where when the mount portion is mounted to the mount surface and during operation of the imaging system, the sprung portion moves relative to the mount surface, an amount of movement of the sprung portion based at least in part on the vibrational tuner.

2. The DVA of claim 1, wherein during operation of the imaging system, the vibrational tuner causes the sprung portion to exhibit one or more vibrational characteristics that match one or more vibrational characteristics of the imaging system.

3. The DVA of claim 2, wherein the vibrational tuner causes the sprung portion to exhibit a vibrational frequency within a threshold range of the vibrational frequency of the imaging system.

4. The DVA of claim 3, wherein the vibrational tuner causes the sprung portion to exhibit a vibrational phase that is out-of-phase of the vibrational phase of the imaging system.

5. The DVA of claim 1, wherein the vibrational tuner is a first vibrational tuner selected from among a plurality of first vibrational tuners, each first vibrational tuner having a different mass.

6. The DVA of claim 5, wherein each first vibrational tuner has a mass within a smaller, first range.

7. The DVA of claim 6, further comprising a second vibrational tuner selected from among a plurality of second vibrational tuners, each second vibrational tuner having a mass within a larger, second range.

8. The DVA of claim 1, wherein the vibrational tuner is coupled between the mount portion and the sprung portion and is configured to bias the sprung portion relative to the mount portion.

9. The DVA of claim 8, wherein the vibrational tuner comprises a biasing member selected from among a plurality of biasing members, where at least two biasing members of the plurality of biasing members have a different stiffness relative to each other.

10. The DVA of claim 1, wherein the mount portion includes a first arm and an opposing, second arm, the first and second arms each having an aperture adapted to receive a respective fastener.

11. A method, comprising:
coupling a dynamic vibration absorber (DVA) comprising a vibrational tuner, a mount portion including one or more apertures, and a sprung portion to a mount surface of an imaging system via the mount portion;
determining a vibration frequency of the DVA while rotating a rotor of the imaging system; and
fine-tuning the vibration frequency of the DVA based on the determined vibration frequency; and
wherein the sprung portion moves relative to the mount surface, an amount of movement of the sprung portion based at least in part on the vibrational tuner.

12. The method of claim 11, wherein the DVA includes a plurality of mass-adjustment portions, and wherein fine-tuning the vibration frequency includes removing, replacing, or adding one or more of the plurality of mass-adjustment portions to or from the DVA.

13. The method of claim 12, wherein fine-tuning the vibration frequency by removing, replacing, or adding one or more of the plurality of mass-adjustment portions comprises fine-tuning the vibration frequency by removing, replacing, or adding a first, lower mass mass-adjustment portion.

14. The method of claim 13, further comprising gross-tuning the vibration frequency by removing, replacing, or adding a second, higher mass mass-adjustment portion to or from the DVA.

15. The method of claim 11, wherein the DVA includes one or more biasing members, and wherein fine-tuning the vibration frequency includes replacing a biasing member of the one or more biasing members the DVA with a biasing member having a different stiffness.

16. A system, comprising:
a gantry;
an x-ray radiation source coupled to the gantry and including an x-ray tube and a housing;
a mount surface; and
a dynamic vibration absorber (DVA) configured to couple to the mount surface of one of the gantry, the x-ray tube, or the housing via a mount portion including one or more apertures, the DVA comprising a sprung portion, and one or more interchangeable elements configured to adjust vibration characteristics of the DVA, wherein during operation of the system, the sprung portion moves relative to the mount surface, an amount of movement of the sprung portion based at least in part on the one or more interchangeable elements.

17. The system of claim 16, wherein the one or more interchangeable elements include one or more mass-adjustment portions.

18. The system of claim 16, wherein the one or more interchangeable elements include one or more biasing members.

19. The system of claim 16, wherein the mount portion and the sprung portion are formed as a unitary piece.

20. The system of claim 16, wherein the DVA is configured to vibrate out-of-phase relative a vibration of the x-ray tube.

* * * * *